United States Patent
Koch et al.

(10) Patent No.: US 10,105,238 B2
(45) Date of Patent: Oct. 23, 2018

(54) EXPANDABLE INTERVERTEBRAL IMPLANTS

(71) Applicant: IMDS LLC, Providence, UT (US)

(72) Inventors: David Koch, North Logan, UT (US); Jason Glad, Nibley, UT (US)

(73) Assignee: IMDS LLC, Providence, UT (US)

( * ) Notice: Subject to any disclaimer, the term of this patent is extended or adjusted under 35 U.S.C. 154(b) by 156 days.

(21) Appl. No.: 15/244,446

(22) Filed: Aug. 23, 2016

(65) Prior Publication Data

US 2017/0056200 A1    Mar. 2, 2017

Related U.S. Application Data

(60) Provisional application No. 62/209,604, filed on Aug. 25, 2015.

(51) Int. Cl.
*A61F 2/44*   (2006.01)
*A61F 2/46*   (2006.01)

(52) U.S. Cl.
CPC .............. *A61F 2/4455* (2013.01); *A61F 2/44* (2013.01); *A61F 2/4611* (2013.01); *A61F 2002/4475* (2013.01); *A61F 2220/0016* (2013.01); *A61F 2250/0004* (2013.01)

(58) Field of Classification Search
CPC ............ A61F 2/4455; A61F 2250/0007; A61F 2250/0004; A61F 2250/0009
See application file for complete search history.

(56) References Cited

U.S. PATENT DOCUMENTS

| | | | |
|---|---|---|---|
| 619,413 | A | 2/1899 | Higgins |
| 4,164,225 | A | 8/1979 | Johnson |
| 4,657,550 | A | 4/1987 | Daher |
| 4,834,757 | A | 5/1989 | Brantigan |
| 4,863,476 | A | 9/1989 | Shepperd |
| 5,059,193 | A | 10/1991 | Kuslich |
| 5,171,278 | A | 12/1992 | Pisharodi |
| 5,290,312 | A | 3/1994 | Kojimoto |
| 5,306,310 | A | 4/1994 | Siebels |
| 5,336,223 | A | 8/1994 | Rogers |

(Continued)

FOREIGN PATENT DOCUMENTS

| | | |
|---|---|---|
| AU | 2013206287 A1 | 7/2013 |
| AU | 2013262504 A1 | 1/2015 |

(Continued)

*Primary Examiner* — Andrew Yang
(74) *Attorney, Agent, or Firm* — Marywood IP Law; G. Jo Hays; Stuart S. Bray

(57) ABSTRACT

Interbody spacers are expandable horizontally and vertically by an application of axial force, and lockable in an expanded configuration. The spacers include support members interconnected to end bodies by pivotable link members. The spacers are introduced between vertebral bodies in a compressed configuration and expanded to fill the intervertebral space and provide support and selective lordotic correction. Graft material may be introduced into the expanded spacer. Provisional and/or supplementary locking means lock the spacers in the expanded configuration. Embodiments of the spacers include symmetrically and asymmetrically configured spacers. Methods of expansion include symmetric expansion or asymmetric expansion along each of two directions.

17 Claims, 24 Drawing Sheets

(56) References Cited

U.S. PATENT DOCUMENTS

| | | |
|---|---|---|
| 5,390,683 A | 2/1995 | Pisharodi |
| 5,405,391 A | 4/1995 | Hednerson |
| 5,425,772 A | 6/1995 | Brantigan |
| 5,443,514 A | 8/1995 | Steffee |
| 5,458,641 A | 10/1995 | Ramirez Jimenez |
| 5,554,191 A | 9/1996 | Lahille |
| 5,571,192 A | 11/1996 | Schonhoffer |
| 5,653,762 A | 8/1997 | Pisharodi |
| 5,653,763 A | 8/1997 | Errico |
| 5,658,335 A | 8/1997 | Allen |
| 5,665,122 A | 9/1997 | Kambin |
| 5,693,100 A | 12/1997 | Pisharodi |
| 5,702,455 A | 12/1997 | Saggar |
| 5,716,415 A | 2/1998 | Steffee |
| 5,776,198 A | 7/1998 | Rabbe |
| 5,782,832 A | 7/1998 | Larsen |
| 5,865,848 A | 2/1999 | Baker |
| 5,980,522 A | 11/1999 | Koros |
| 5,989,290 A | 11/1999 | Biedermann |
| 6,015,436 A | 1/2000 | Schonhoffer |
| 6,039,761 A | 3/2000 | Li |
| 6,045,579 A | 4/2000 | Hochshuler |
| 6,080,193 A | 6/2000 | Hochshuler |
| 6,093,207 A | 7/2000 | Pisharodi |
| 6,102,950 A | 8/2000 | Vaccaro |
| 6,117,174 A | 9/2000 | Nolan |
| 6,126,689 A | 10/2000 | Brett |
| 6,126,869 A | 10/2000 | Haaland |
| 6,129,763 A | 10/2000 | Chauvin |
| 6,159,244 A | 12/2000 | Suddaby |
| 6,174,334 B1 | 1/2001 | Suddaby |
| 6,176,881 B1 | 1/2001 | Schär |
| 6,183,517 B1 | 2/2001 | Suddaby |
| 6,190,413 B1 | 2/2001 | Sutcliffe |
| 6,190,414 B1 | 2/2001 | Young |
| 6,193,755 B1 | 2/2001 | Metz Stavenhagen |
| 6,193,756 B1 | 2/2001 | Studer |
| 6,193,757 B1 | 2/2001 | Foley |
| 6,200,348 B1 | 3/2001 | Biedermann |
| 6,214,050 B1 | 4/2001 | Huene |
| 6,296,647 B1 | 10/2001 | Robioneck |
| 6,299,644 B1 | 10/2001 | Vanderschot |
| 6,332,895 B1 | 12/2001 | Suddaby |
| 6,395,034 B1 | 5/2002 | Suddaby |
| 6,413,278 B1 | 7/2002 | Marchosky |
| 6,419,705 B1 | 7/2002 | Erickson |
| 6,436,140 B1 | 8/2002 | Liu |
| 6,454,806 B1 | 9/2002 | Cohen |
| 6,491,724 B1 | 12/2002 | Ferree |
| 6,562,074 B2 | 5/2003 | Gerbec |
| 6,582,431 B1 | 6/2003 | Ray |
| 6,648,917 B2 | 11/2003 | Gerbec |
| 6,660,038 B2 | 12/2003 | Boyer, II |
| 6,666,891 B2 | 12/2003 | Boehm, Jr. |
| 6,685,742 B1 | 2/2004 | Jackson |
| 6,706,070 B1 | 3/2004 | Wagner |
| 6,709,458 B2 | 3/2004 | Michelson |
| 6,723,126 B1 | 4/2004 | Berry |
| 6,730,126 B2 | 5/2004 | Boehm, Jr. |
| 6,746,484 B1 | 6/2004 | Liu |
| 6,833,006 B2 | 12/2004 | Foley |
| 6,852,129 B2 | 2/2005 | Gerbec |
| 6,863,673 B2 | 3/2005 | Gerbec |
| 6,893,464 B2 | 5/2005 | Kiester |
| 7,070,598 B2 | 7/2006 | Lim |
| 7,513,900 B2 | 4/2009 | Carrison |
| 7,625,377 B2 | 12/2009 | Veldhuizen |
| 7,799,081 B2 | 9/2010 | McKinley |
| 7,824,427 B2 | 11/2010 | Perez-Cruet |
| 7,846,206 B2 | 12/2010 | Oglaza |
| 7,879,098 B1 | 2/2011 | Simmons, Jr. |
| 7,922,729 B2 | 4/2011 | Michelson |
| 8,012,207 B2 | 9/2011 | Kim |
| 8,097,018 B2 | 1/2012 | Malandain |
| 8,097,035 B2 | 1/2012 | Glenn |
| 8,109,972 B2 | 2/2012 | Zucherman |
| 8,110,004 B2 | 2/2012 | Valdevit |
| 8,152,837 B2 | 4/2012 | Altarac |
| 8,317,798 B2 | 11/2012 | Lim |
| 8,323,344 B2 | 12/2012 | Galley |
| 8,409,291 B2 | 4/2013 | Blackwell |
| 8,491,657 B2 | 7/2013 | Attia |
| 8,496,709 B2 | 7/2013 | Schell |
| 8,506,635 B2 | 8/2013 | Palmatier |
| 8,541,355 B2 | 9/2013 | Fleckenstein |
| 8,568,481 B2 | 10/2013 | Olmos |
| 8,579,907 B2 | 11/2013 | Lim |
| 8,628,576 B2 | 1/2014 | Triplett |
| 8,652,174 B2 | 2/2014 | Gabelberger |
| 8,663,329 B2 | 3/2014 | Ernst |
| 8,678,576 B2 | 3/2014 | Edombingo |
| 8,685,095 B2 | 4/2014 | Miller |
| 8,777,993 B2 | 7/2014 | Siegal |
| 8,778,027 B2 | 7/2014 | Medina |
| 8,808,385 B1 | 8/2014 | Smith |
| 8,900,305 B2 | 12/2014 | Stad |
| 8,926,704 B2 | 1/2015 | Glerum |
| 8,940,048 B2 | 1/2015 | Butler |
| 9,060,876 B1 * | 6/2015 | To .................... A61F 2/442 |
| 9,308,099 B2 | 4/2016 | Triplett |
| 9,445,918 B1 | 9/2016 | Lin et al. |
| 2001/0032017 A1 | 10/2001 | Alfaro |
| 2002/0010511 A1 | 1/2002 | Michelson |
| 2003/0229355 A1 | 12/2003 | Keller |
| 2004/0002758 A1 | 1/2004 | Landry |
| 2004/0034430 A1 | 2/2004 | Falahee |
| 2005/0177235 A1 | 8/2005 | Baynham |
| 2005/0182416 A1 | 8/2005 | Lim |
| 2005/0222681 A1 | 10/2005 | Richley |
| 2005/0234555 A1 | 10/2005 | Sutton |
| 2005/0278036 A1 | 12/2005 | Leonard |
| 2006/0142858 A1 | 6/2006 | Colleran |
| 2006/0167547 A1 | 7/2006 | Suddaby |
| 2007/0043440 A1 | 2/2007 | William |
| 2007/0049935 A1 | 3/2007 | Edidin |
| 2007/0067034 A1 | 3/2007 | Chirico |
| 2007/0118222 A1 | 5/2007 | Lang |
| 2007/0198089 A1 | 8/2007 | Moskowitz |
| 2007/0219634 A1 | 9/2007 | Greenhalgh |
| 2007/0260315 A1 | 11/2007 | Foley |
| 2007/0282449 A1 | 12/2007 | de Villiers |
| 2008/0033440 A1 | 2/2008 | Moskowitz |
| 2008/0045968 A1 | 2/2008 | Yu |
| 2008/0082167 A1 | 4/2008 | Edidin |
| 2008/0108990 A1 | 5/2008 | Mitchell |
| 2008/0114367 A1 | 5/2008 | Meyer |
| 2008/0167657 A1 | 7/2008 | Greenhalgh |
| 2008/0183204 A1 * | 7/2008 | Greenhalgh ........ A61B 17/8858 606/198 |
| 2008/0195152 A1 | 8/2008 | Altarac |
| 2008/0219604 A1 | 9/2008 | Chen |
| 2008/0221686 A1 | 9/2008 | Ferree |
| 2008/0243255 A1 | 10/2008 | Butler |
| 2008/0249604 A1 | 10/2008 | Donovan |
| 2008/0281346 A1 | 11/2008 | Greenhalgh |
| 2008/0288072 A1 | 11/2008 | Kohm |
| 2008/0288078 A1 | 11/2008 | Kohm |
| 2008/0319549 A1 | 12/2008 | Greenhalgh |
| 2009/0076607 A1 | 3/2009 | Aalsma |
| 2009/0157084 A1 | 6/2009 | Aalsma |
| 2009/0198338 A1 | 8/2009 | Phan |
| 2009/0222093 A1 | 9/2009 | Liu |
| 2009/0222100 A1 | 9/2009 | Cipoletti |
| 2009/0281628 A1 | 11/2009 | Oglaza |
| 2010/0082109 A1 | 4/2010 | Greenhalgh |
| 2010/0185291 A1 | 7/2010 | Jimenez |
| 2010/0249720 A1 | 9/2010 | Biyani |
| 2010/0286783 A1 | 11/2010 | Lechmann |
| 2010/0305705 A1 | 12/2010 | Butler |
| 2010/0318127 A1 | 12/2010 | Phan |
| 2011/0004307 A1 | 1/2011 | Ahn |
| 2011/0125270 A1 | 5/2011 | Paul |
| 2011/0172774 A1 | 7/2011 | Varela |
| 2011/0270396 A1 | 11/2011 | Leibowitz |

(56) References Cited

U.S. PATENT DOCUMENTS

| | | |
|---|---|---|
| 2011/0276141 A1 | 11/2011 | Caratsch |
| 2011/0282453 A1 | 11/2011 | Greenhalgh |
| 2011/0319997 A1 | 12/2011 | Glerum |
| 2012/0004732 A1 | 1/2012 | Goel |
| 2012/0053642 A1 | 3/2012 | Lozier |
| 2012/0071977 A1 | 3/2012 | Oglaza |
| 2012/0083887 A1 | 4/2012 | Purcell et al. |
| 2012/0083889 A1 | 4/2012 | Purcell |
| 2012/0123546 A1 | 5/2012 | Medina |
| 2012/0136442 A1 | 5/2012 | Kleiner |
| 2012/0150241 A1 | 6/2012 | Ragab |
| 2012/0185047 A1 | 7/2012 | Wooley |
| 2012/0185049 A1 | 7/2012 | Varela |
| 2012/0215313 A1 | 8/2012 | Saidha |
| 2012/0215316 A1 | 8/2012 | Mohr |
| 2012/0226357 A1 | 9/2012 | Varela |
| 2012/0245691 A1 | 9/2012 | Reimels |
| 2013/0079882 A1 | 3/2013 | Wolfe |
| 2013/0079883 A1 | 3/2013 | Butler |
| 2013/0144391 A1 | 6/2013 | Siegal |
| 2013/0158669 A1 | 6/2013 | Sungarian |
| 2013/0190876 A1 | 7/2013 | Drochner |
| 2013/0310939 A1 | 11/2013 | Fabian |
| 2013/0325128 A1 | 12/2013 | Perloff |
| 2014/0031940 A1 | 1/2014 | Banouskou |
| 2014/0039622 A1 | 2/2014 | Glerum |
| 2014/0052253 A1 | 2/2014 | Perloff |
| 2014/0088714 A1 | 3/2014 | Miller |
| 2014/0121774 A1 | 5/2014 | Glerum |
| 2014/0128977 A1 | 5/2014 | Glerum |
| 2014/0172106 A1 | 6/2014 | To |
| 2014/0188224 A1 | 7/2014 | Dmuschewsky |
| 2014/0194991 A1 | 7/2014 | Jimenez |
| 2014/0194992 A1 | 7/2014 | Medina |
| 2014/0257484 A1 | 9/2014 | Flower |
| 2014/0277490 A1 | 9/2014 | Perloff |
| 2014/0379086 A1 | 12/2014 | Elahinia |
| 2015/0012098 A1 | 1/2015 | Eastlack |
| 2015/0018951 A1 | 1/2015 | Loebl |
| 2015/0073552 A1 | 3/2015 | To |
| 2016/0199194 A1 | 7/2016 | Slater |

FOREIGN PATENT DOCUMENTS

| | | |
|---|---|---|
| CA | 2567274 C | 11/2014 |
| EP | 0260044 A1 | 3/1988 |
| EP | 1006956 A1 | 6/2000 |
| EP | 2693989 A1 | 2/2014 |
| EP | 2729092 A1 | 5/2014 |
| EP | 2793760 A1 | 10/2014 |
| EP | 3038566 A1 | 7/2016 |
| WO | WO1998034568 A1 | 8/1998 |
| WO | WO2000025706 A1 | 5/2000 |
| WO | WO2002076335 A2 | 10/2002 |
| WO | WO2003032812 A2 | 4/2003 |
| WO | WO2005112834 A2 | 12/2005 |
| WO | WO2008070863 A2 | 6/2008 |
| WO | WO2009037509 A1 | 3/2009 |
| WO | WO2009092102 A1 | 7/2009 |
| WO | WO2010078468 A2 | 7/2010 |
| WO | WO2010105181 A1 | 9/2010 |
| WO | WO2012047712 A1 | 4/2012 |
| WO | WO2012112596 A1 | 8/2012 |
| WO | WO2012141715 A1 | 10/2012 |
| WO | WO2013052807 A2 | 4/2013 |
| WO | WO2013109346 A1 | 7/2013 |
| WO | WO2013173767 A1 | 11/2013 |
| WO | WO2014144696 | 9/2014 |
| WO | WO2014151162 A1 | 9/2014 |
| WO | WO2014164625 A1 | 10/2014 |
| WO | WO2015009998 A1 | 1/2015 |
| WO | WO2015031291 A1 | 3/2015 |
| WO | WO2015063719 A1 | 3/2015 |
| WO | WO2017035155 A1 | 3/2017 |

\* cited by examiner

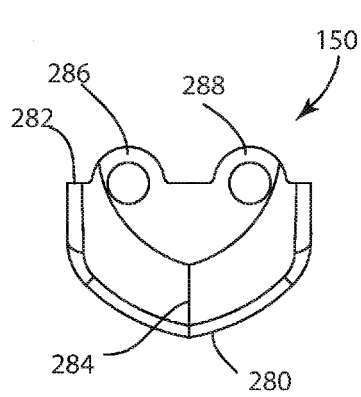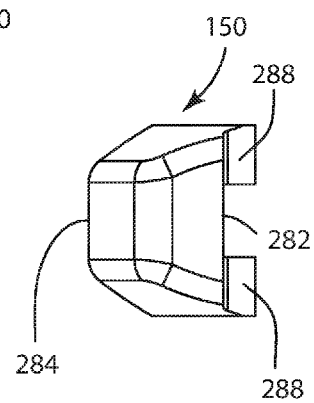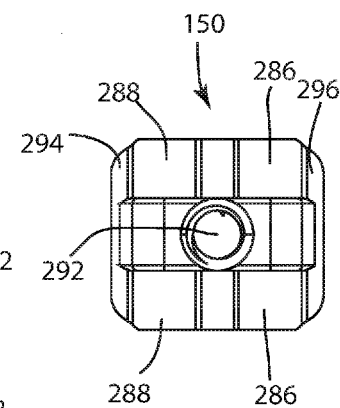
Fig. 6A  Fig. 6B  Fig. 6C
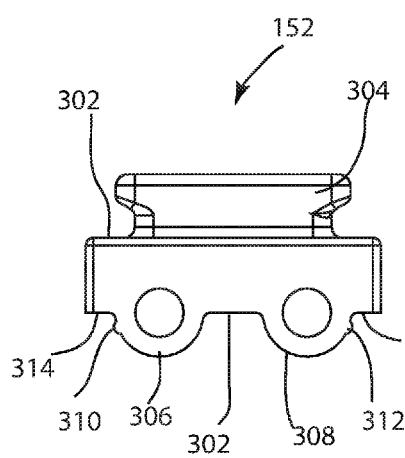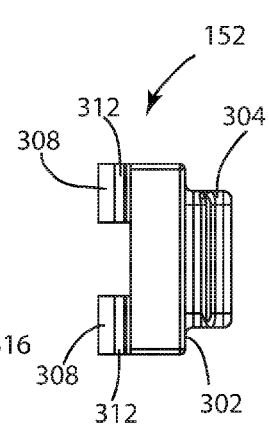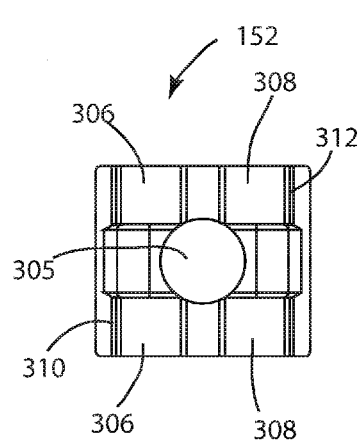
Fig. 7A  Fig. 7B  Fig. 7C

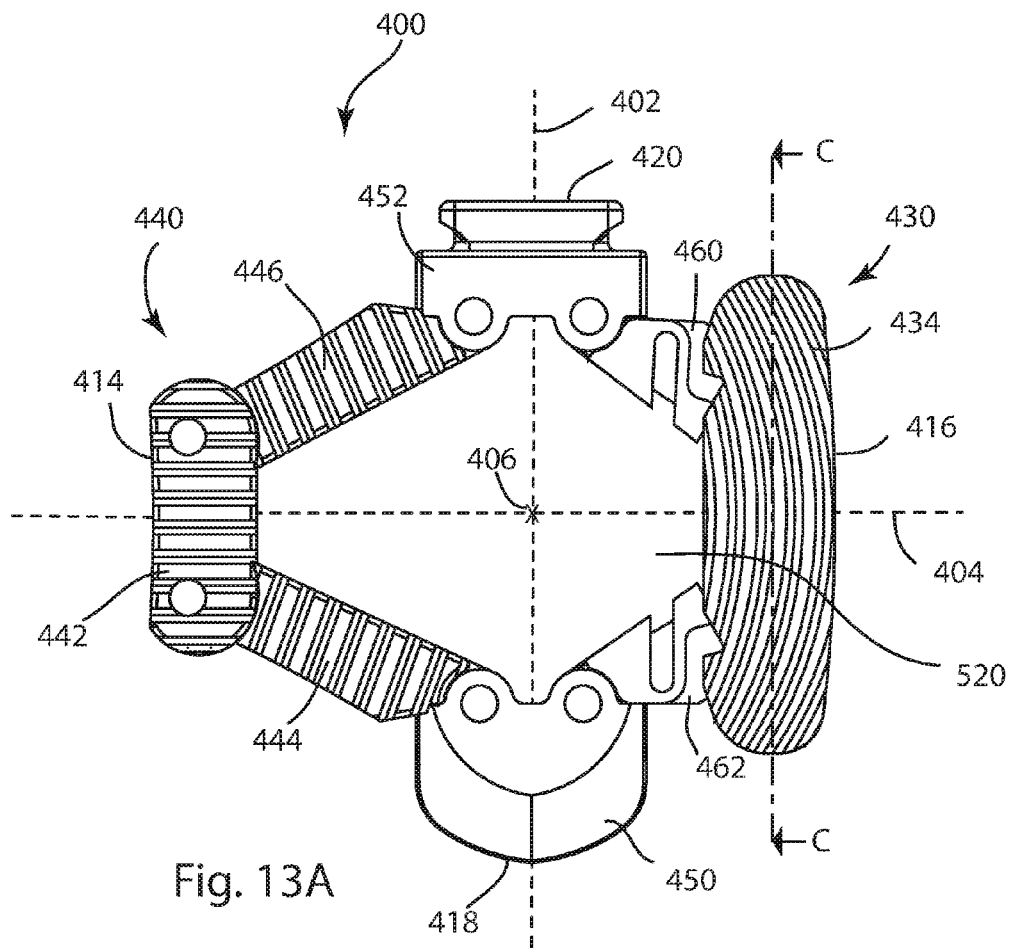
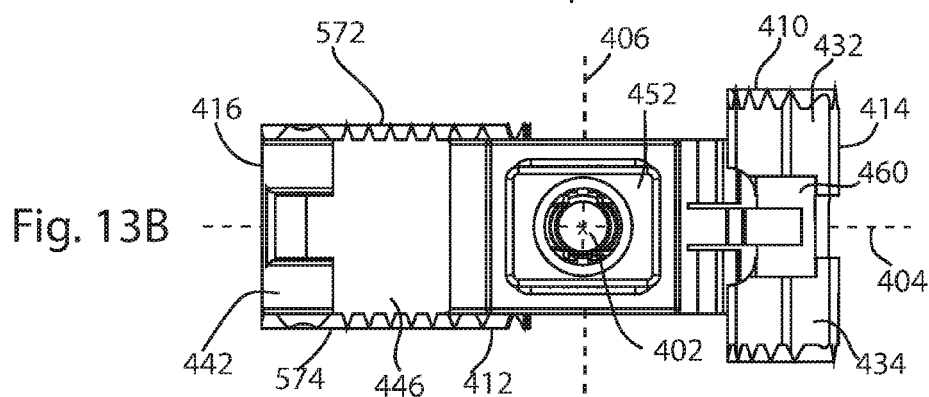

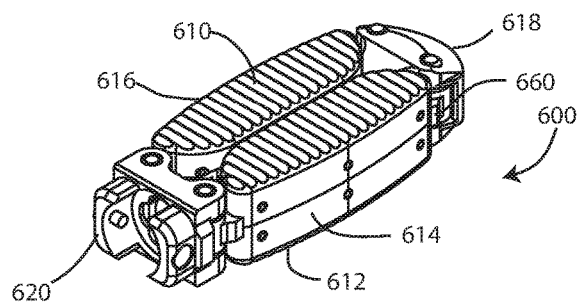
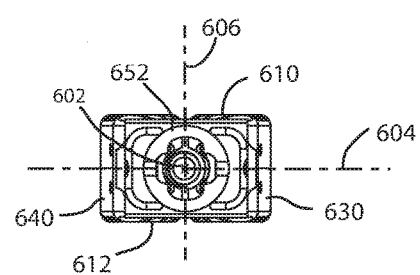
Fig. 16A　　　　　　　　　Fig. 16B
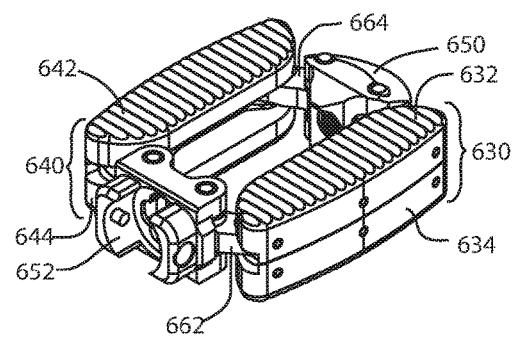
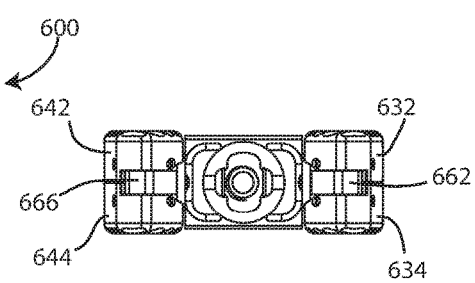
Fig. 16C　　　　　　　　　Fig. 16D
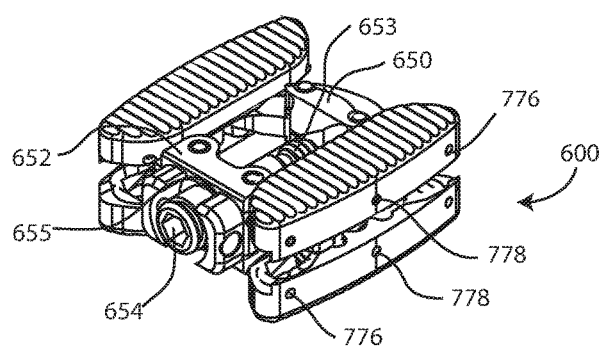
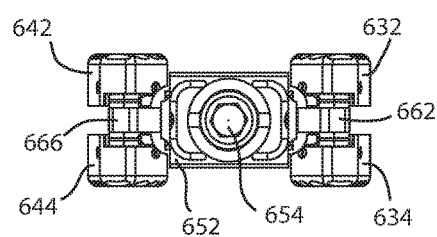
Fig. 16E　　　　　　　　　Fig. 16F

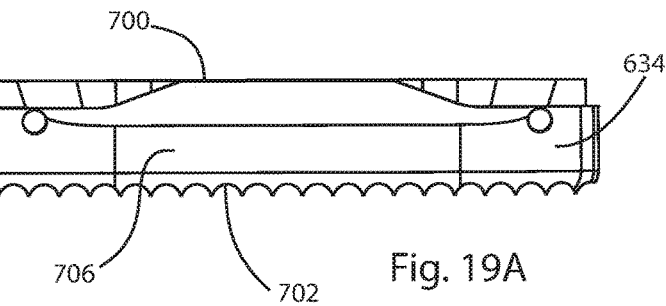
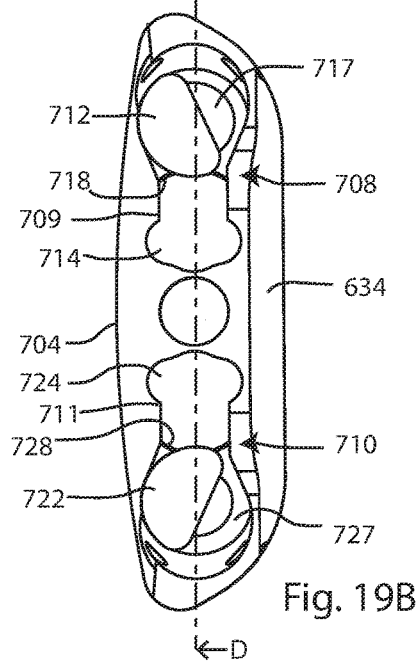
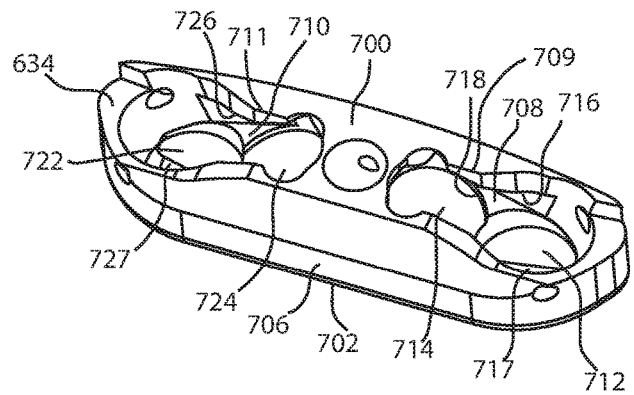
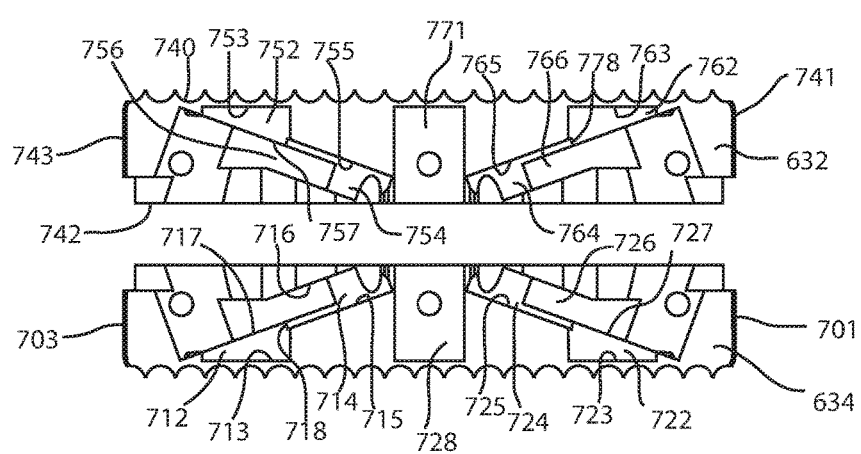
Fig. 19A
Fig. 19C
Fig. 19B
Fig. 19D

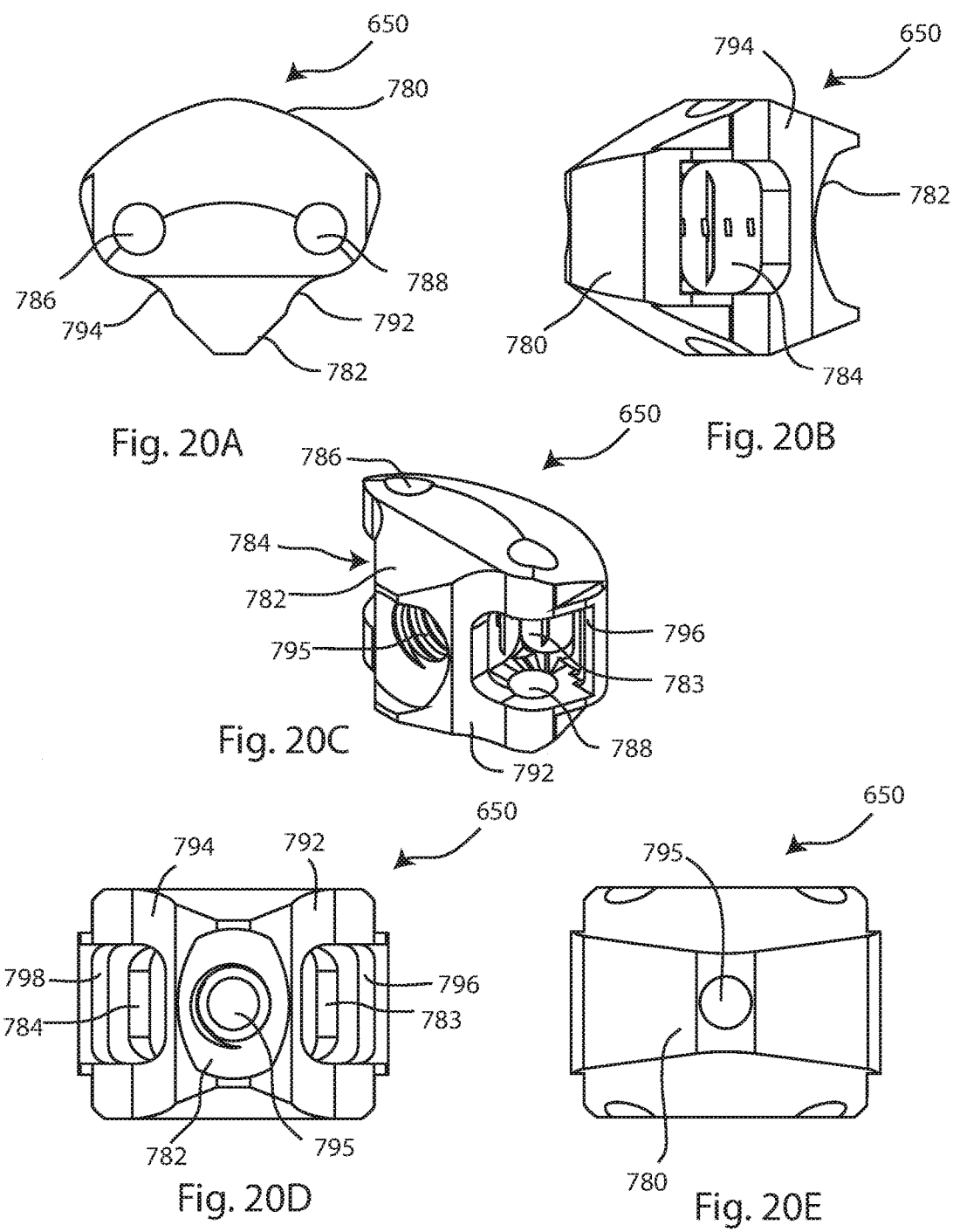

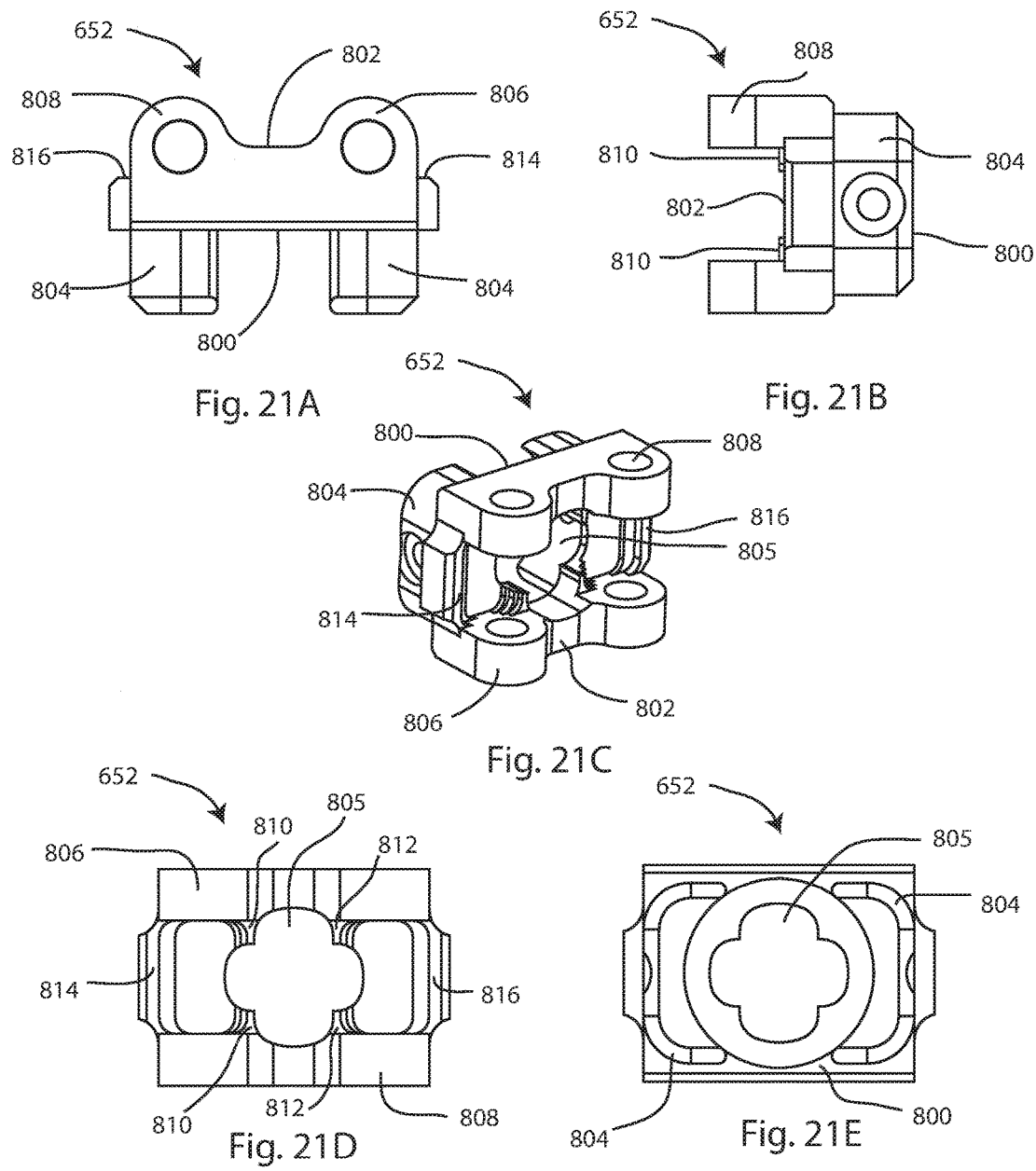

EXPANDABLE INTERVERTEBRAL IMPLANTS

CROSS-REFERENCE TO RELATED APPLICATIONS

This application claims the benefit of pending U.S. Provisional Patent Application No. 62/209,604, filed Aug. 25, 2015, and is entitled EXPANDABLE INTERVERTEBRAL IMPLANT.

The above-identified document is incorporated herein by reference.

FIELD OF THE INVENTION

This invention generally relates to the field of spinal surgery, and more particularly, to spinal cages used in fusing adjacent vertebrae.

BACKGROUND OF THE INVENTION

In a vertebrate spine, the spinal disc and/or vertebral bodies may be displaced or damaged due to trauma, disease, degenerative defects, or wear over an extended period of time. One result of this displacement or damage to a spinal disc or vertebral body may be chronic back pain. A common procedure for treating damage or disease of the spinal disc or vertebral body may involve partial or complete removal of an intervertebral disc. An implant, which may be referred to as an interbody spacer, or intervertebral implant, can be inserted into the cavity created where the intervertebral disc was removed to help maintain height of the spine and/or restore stability to the spine. An interbody spacer may also provide a lordotic correction to the curvature of the spine. An example of an interbody spacer that has been commonly used is a fixed dimension cage, which typically is packed with bone and/or bone-growth-inducing materials.

One drawback of spacers known in the art is that they can be of fixed height and/or footprint, and may not provide adequate or precise height restoration and support between affected vertebral bodies. Fixed size cages can also require more invasive procedures for implantation, due to their necessarily larger pre-implantation size. Accordingly, there is a need for an intervertebral implant which can be inserted along one axis, and be expanded both horizontally and vertically to provide intervertebral support and lordotic correction.

BRIEF DESCRIPTION OF THE DRAWINGS

Exemplary embodiments of the invention will be best understood by reference to the drawings, wherein like parts are designated by like numerals throughout. It will be readily understood that the components of the invention, as generally described and illustrated in the Figures herein, could be arranged and designed in a wide variety of different configurations. Thus, the following more detailed description of the embodiments of the apparatus, system, and method, as represented in FIGS. 1 through 27E, is not intended to limit the scope of the invention, as claimed in this or any other application claiming priority to this application, but is merely representative exemplary of exemplary embodiments of the invention. Embodiments of the invention are depicted in the following figures:

FIG. 6A is a top down view of a first end body of the spacer of FIG. 1, FIG. 6B is a side view of the end body of FIG. 6A, and FIG. 6C is an inner side view of the of the end body of FIG. 6A;

FIG. 7A is a top down view of a second end body of the spacer of FIG. 1, FIG. 7B is a side view of the end body of FIG. 7A, and FIG. 7C is an inner side view of the of the end body of FIG. 6A;

FIG. 13A is a bottom view of the interbody spacer of FIG. 11 in the expanded configuration; FIG. 13B is a first end view of the interbody spacer of FIG. 11 in the expanded configuration;

FIG. 16A is an isometric view of an alternative embodiment of an interbody spacer in a collapsed configuration; FIG. 16B is a back end view of the interbody spacer of FIG. 16A; FIG. 16C is an isometric view of the interbody spacer of FIG. 16A in a laterally expanded configuration; FIG. 16D is a back end view of the interbody spacer of FIG. 16C; FIG. 16E is an isometric view of the interbody spacer of FIG. 16A in a laterally and vertically expanded configuration; and FIG. 16F is a back end view of the interbody spacer of FIG. 16E;

FIG. 19A is an interior side view of a lower support body of the interbody spacer of FIG. 16A; FIG. 19B is a top down view of the lower support body of FIG. 19A; FIG. 19C is an isometric view of the lower support body of FIG. 19A; and FIG. 19D is an cross-sectional view of the lower support body of FIG. 16A taken along line D-D in FIG. 19B and a cross-sectional view of an upper support body of the interbody spacer of FIG. 16A taken along an approximate midline of the upper support body;

FIG. 20A is a top down view of a first end body of the interbody spacer of FIG. 16A; FIG. 20B is a side view of the first end body of FIG. 20A; FIG. 20C is an isometric view of the first end body of FIG. 20A; FIG. 20D is an inner side view of the first end body of FIG. 20A; and FIG. 20E is an outer side view of the first end body of FIG. 20A;

FIG. 21A is an outer side view of a second end body of the interbody spacer of FIG. 16A; FIG. 21B is an inner side view of the first end body of FIG. 21A; FIG. 21C is an isometric view of the first end body of FIG. 21A; FIG. 21D is a side view of the first end body of FIG. 21A; and FIG. 21E is an top down view of the first end body of FIG. 21A;

DETAILED DESCRIPTION OF THE EMBODIMENTS

Disclosed herein are interbody spacers which are expandable from a collapsed or closed configuration to an expanded or open configuration by means of horizontal and/or vertical expansion. Expansion of the spacer may take place in situ after placement in between two vertebral bodies, and bone graft or other materials may be inserted into the open space during or after placement and expansion. The impetus to expand the spacer may be provided by a single application of axial force along a longitudinal spacer axis. The intervertebral spacers disclosed herein include symmetrical and asymmetrical embodiments, and embodiments which may expand symmetrically and/or asymmetrically. One or more embodiments may include means for lordotic correction. Lordotic correction may be provided inherently by angulation of spacer body surfaces, and/or by asymmetrical spacer expansion.

Figure 1A:
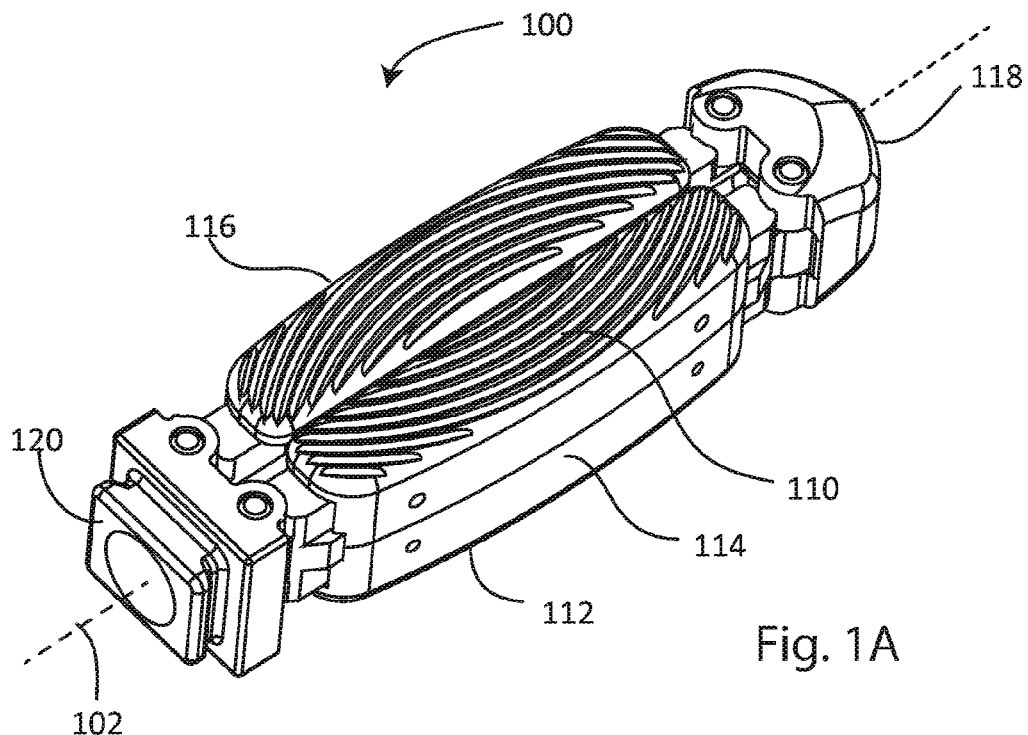
FIG. 1A is an isometric view of an embodiment of an interbody spacer in a collapsed configuration.

Referring to FIGS. 1A through 3B, an interbody spacer 100, which may also be referred to as a device, cage, insert, or implant, is expandable from the collapsed, or compact configuration seen in FIG. 1A, along a first axis and a second axis. The spacer 100 has a lengthwise spacer axis 102, and may be expandable in a first direction along a first axis 104 which may be a horizontal or lateral expansion axis, to a horizontally expanded configuration seen in FIG. 2A. The device may be further expanded in a second direction along a second axis 106, which may be a vertical expansion axis, to the horizontally and vertically expanded configuration seen in FIG. 3. Axes 104, 106 may be perpendicular to each other and perpendicular to spacer axis 102. When implanted between two vertebral bodies in a portion of a spine, the spacer 100 is expandable horizontally, or substantially anterior-posteriorly, along the first axis 104, and vertically, or cephalad-caudally, along the second axis 106. A single axial force acting along the spacer axis 102 may provide the expansion force for both the horizontal and vertical expansion. The spacer 100 may be bilaterally symmetrical with respect to a vertical plane extending along spacer axis 102, and may be bilaterally symmetrical with respect to a horizontal plane extending along spacer axis 102. In an alternate embodiment, the spacer may be expandable medial-laterally. In other embodiments, the spacer may be asymmetrically expandable anterior-posteriorly, cephalad-caudally, and/or medial-laterally. It is understood any one of the spacers disclosed within may also be implanted non-parallel to the sagittal plane of the vertebral bodies, in which instance horizontal spacer expansion may not be strictly anterior-posterior or medial-lateral.

Figure 1B:
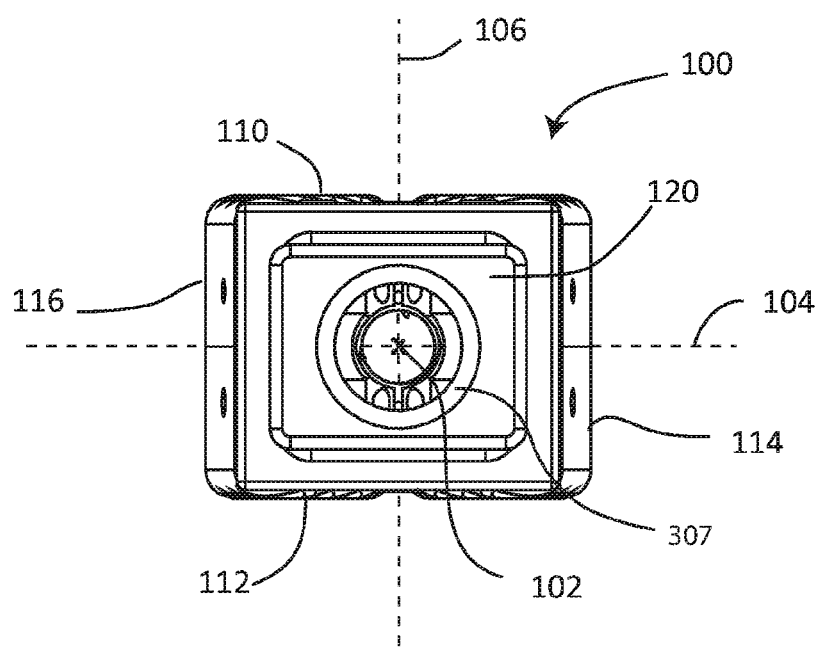
FIG. 1B is an end view of the interbody spacer of FIG. 1B.

Referring to FIGS. 1A and 1B, the spacer 100 includes an upper surface 110 and a lower surface 112 separated by a first side 114 and a second side 116. A first end 118 and a second end 120 are separated by the upper and lower surface and first and second sides.

Referring to FIGS. 1A through 4, the interbody spacer comprises a set of bodies pivotably linked together, allowing the bodies to articulate relative to one another. A first support member 130 includes a first upper body 132 and a first lower body 134. A second support member 140 includes a second upper body 142 and a second lower body 144. A first end body 150 is pivotably linked to the first and second support members 130, 140 toward the first end 118, and a second end body 152 is pivotably linked to the first and second support members 130, 140 toward the second end 120. The upper and lower bodies may be mirror images of one another, as may the first and second support members. In an alternate embodiment the first and second support members 130 and 140 may be of differing proportions and/or configuration in order to provide asymmetric expansion.

Figure 4:
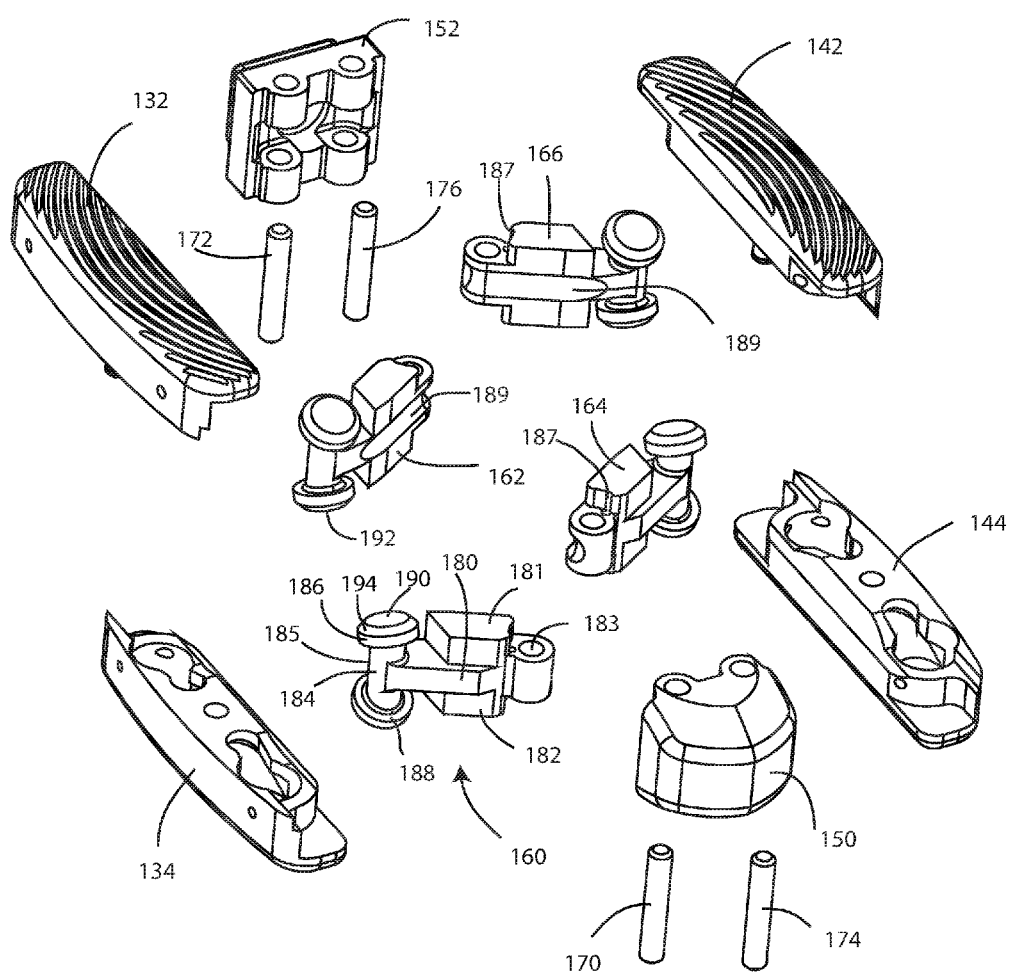
FIG. 4 is an exploded isometric view of the interbody spacer of FIG. 1.
Figure 5A:
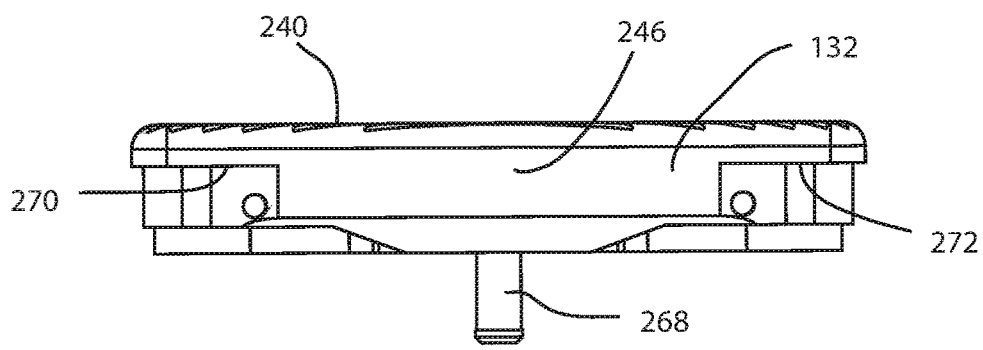
FIG. 5A is a side view of an upper body of the interbody spacer of FIG. 1.
Figure 5B:
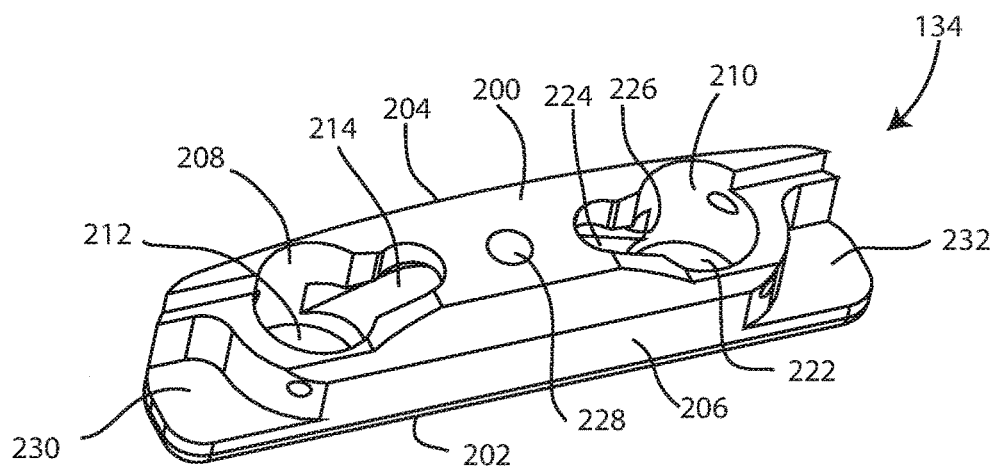
FIG. 5B is an isometric view of a lower body of the interbody spacer of FIG. 1.
Figure 5C:
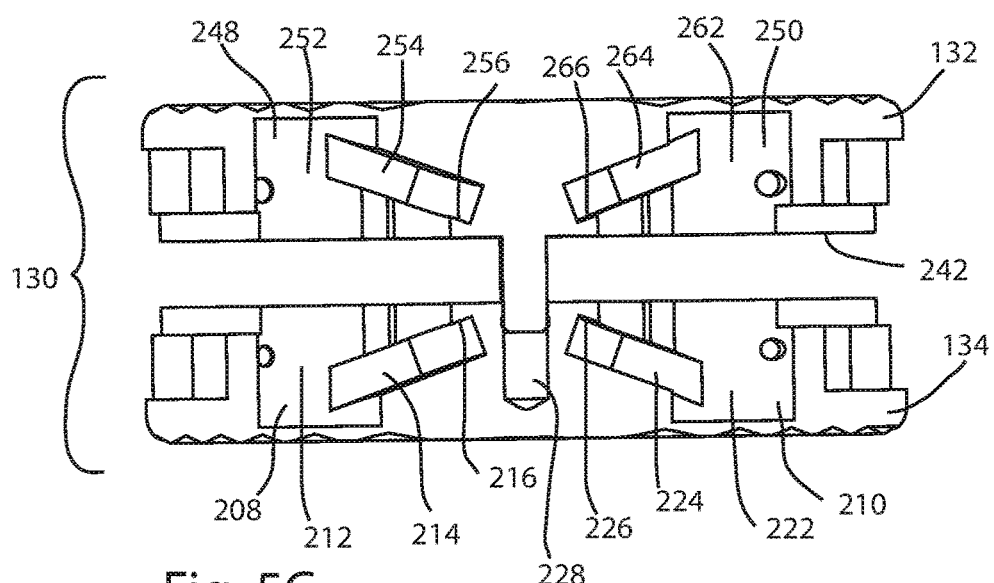
FIG. 5C is a side cross-sectional view of the upper and lower bodies of FIGS. 5A and 5B.

Turning to FIG. 4, additional components of the spacer 100 may be seen. A plurality of links 160, 162, 164, 166 link the support members 130, 140 to the end bodies 150, 152. Link 160 joins first end body 118 to upper and lower bodies 132, 134, via a pin 170. Link 162 joins second end body 120 to the opposite ends of upper and lower bodies 132, 134, via a pin 172. Similarly, link 164 joins first end body 118 to upper and lower bodies 142, 144, via a pin 174. Link 166 joins second end body 120 to the opposite ends of upper and lower bodies 142, 144 via a pin 176.

Each link 160, 162, 164, 166 includes a pivot member which is generally shaped as a spool, in the embodiment depicted. These links may alternately take on other shapes such as cylinders with sloped ends or two generally spherical ends connected by a post. Link 160 is described herein in further detail, but it is appreciated that the description also applies to the other links 162, 164, 166. Link 160 includes a link body 180, which is aligned along a horizontal plane which may be parallel to spacer axis 102 when the spacer is properly assembled. An upper support block 181 is on an upper side of link body 180, opposite a lower support block 182 on the lower side of the link body. An open bore 183 is formed on link body 180 for rotatably receiving pin 170. A locking recess 187 may be formed on the link body to facilitate locking with one of the end bodies, to prevent unintended movement out of the horizontally expanded configuration. A channel 189 may be recessed into the link body to provide passage for instrumentation and/or allograft or other materials. Opposite the open bore, a spool 184 includes a cylindrical stem 185 which supports an upper head 186 and a lower head 188. Other embodiments may include non-cylindrical stems. Upper head 186 includes an upper ramped surface 190, and lower head 188 includes a lower ramped surface 192. Upper and lower ramped surfaces 190, 192 are non-parallel with respect to each other. Each ramped surface 190, 192 may be angled in a range of 0° to 60° relative to the horizontal plane of the link body 180. In an exemplary embodiment, the ramped surfaces may be at an angle of 20° to the horizontal plane of the link body 180. Each head 186, 188 may be of a larger diameter than the cylindrical stem 185. A chamfer 194 may encircle the upper head 186 adjacent the ramped surface 190; similarly a chamfer 196 may encircle the upper head 188 adjacent the ramped surface 192. The chamfers 194, 196 may act as guide surfaces as the spacer 100 transitions from horizontal expansion to vertical expansion.

Support member 130 includes upper and lower bodies 132, 134. First lower body 134 is described herein in further detail, but it is appreciated that the description also applies to the second lower body 144, which may be a mirror image of first lower body 134. Referring to FIGS. 3B, 5A-5C, each upper and lower body is generally elongated and rectangular in footprint, although their perimeters and edges may be rounded to promote easier insertion into the intervertebral space and to prevent damage to surrounding tissues. Depressed into the upper face 200 are a first receptacle 208 and a second receptacle 210. The first receptacle 208 includes a cylindrical portion 212 and a ramped portion 214 with a ramped lower surface. An undercut 216 is formed in the ramped portion 214 away from the cylindrical portion and toward the center of the lower body. The second receptacle 210 may be a mirror image of the first receptacle, and includes a cylindrical portion 222, a ramped portion 224 with a ramped lower surface, and an undercut 226. Each ramped surface may be angled in a range of 0° to 60° relative to the horizontal plane of the lower body 134. In an exemplary embodiment, the ramped surfaces may be at an angle of 20° to the horizontal plane of the lower body 134. A blind bore 228 extends into the body 134 between the receptacles. Recesses 230, 232 in the upper face 200 on opposite ends of the lower body 134, receive portions of links 160, 162 when the implant is in the collapsed configuration as in FIG. 1A.

Upper body 132 is described herein in further detail, but it is appreciated that the description also applies to the other upper body 142, which may be a mirror image of upper body 132. Upper body 132 includes an upper face 240 and a lower face 242, separated by an outer face 244 and an inner face 246. Depressed into the lower face 242 is a first receptacle 248 and a second receptacle 250. The first receptacle 248 includes a cylindrical portion 252 and a ramped portion 254 with a ramped upper surface. The ramped portions 214, 224, 254, 264 may also be referred to as expansion slots. An undercut 256 is formed in the ramped portion 254 away from the cylindrical portion and toward the center of the upper body. Each ramped surface may be angled in a range of 0° to 60° relative to the horizontal plane of the upper body 132. In an exemplary embodiment, the ramped surfaces may be at an angle of 20° to the horizontal plane of the upper body 132. The second receptacle 250 may be a mirror image of the first receptacle, and includes a cylindrical portion 262, a ramped portion 264, and an undercut 266. A peg 268 protrudes from the body 132 between the receptacles.

When the spacer 100 is properly assembled, pegs 268 are received in blind bores 228 to provide proper alignment of upper and lower bodies, provide support in the collapsed configuration, and provide stability. Recesses 270, 272 in the lower face 242 on opposite ends of the upper body 132 receive portions of links 160, 162 when the implant is in the collapsed configuration as in FIG. 1A. Upper face 240 of upper body 132, and lower face 242 of lower body 134 may be exteriorly facing when the spacer 100 is properly implanted, and may include ridges, furrows, points, surface roughening, or other surface treatments to facilitate engagement with the adjacent vertebral bodies. In an alternate embodiment the first and second support members 130 and 140 may be of differing length, proportion and/or configuration, and one of the members may not expand vertically in order to provide asymmetric vertical expansion.

Referring to FIGS. 6 and 7, further details of the end bodies are shown. First end body 150 includes a leading surface 280 and an inner side 282. In the embodiment shown, the leading surface 280 is smooth and bullet-nosed with a leading edge 284 to facilitate insertion into the intervertebral space. The inner side 282 includes connection features 286, 288 for connection to links 162, 166 via pins 172, 176 to form two rotatable end joints 290. It is appreciated that other connection features and/or joint types could be used to achieve the same result within the scope of the invention. In the embodiment shown, each end joint 290 may rotate open up to 60° to provide horizontal expansion. In other embodiments, the end joint may rotate in a range from 20° to 100°. A threaded bore 292 extends partially into the first end body 150 from the inner side 282, to provide connection with insertion and deployment instrumentation. The threaded bore 292 may be perpendicular to the rotation axes of the connection features 286, 288. Stop faces 294, 296 may prevent over-expansion of device 100 by interaction with links 162, 166. The entrance to bore 292 may be further recessed into inner side 282 than are the stop faces.

Second end body 152 includes an exterior face 300 and an inner side 302. The exterior face 300 may include a protruding boss 304, which may facilitate engagement with instrumentation. A bore 305 extends through the second end body 152 between and in communication with the exterior face 300 and the inner side 302. The bore 305 may be non-tapped and may allow access for instrumentation. A lip 307, visible in FIG. 1B, encircles bore 305 near the inner side 302 and may engage with instrumentation. In other embodiments, the bore 305 may be threaded or include other features for engagement with instrumentation. The inner side 302 includes connection features 306, 308 for connection to links 160, 164 via pins 170, 174 to form rotatable end joints 290. The bore 305 may be perpendicular to the rotation axes of the connection features 306, 308. Each connection feature 306, 308 may include a locking feature to hold the device 100 open once it has been horizontally expanded. Locking features 310, 312 are ridges formed on an outer surface of the connection features 306, 308, respectively. When the device 100 is horizontally expanded, the locking feature 310 may snap into the locking recess 187 on link 160 to hold the device 100 horizontally open in a rigid open position and prevent unintended collapse into the collapsed configuration. It is appreciated that similar locking features could also be included on first end body 150, or that other types of tabs, latches, inserts, set screws, or locking features could be included on the device to keep the device rigidly locked open and prevent unintentional collapse. Stop faces 314, 316 may prevent over-expansion of device 100 by interaction with links 160, 164.

In a method of use, a patient may be prepared by performing a discectomy between two target intervertebral bodies. A lateral or anterior approach may be used. The vertebral bodies may be distracted, and spacer 100 mounted on an appropriate insertion instrument and inserted into the prepared space in between the vertebral bodies. In one example, the spacer 100 is mounted on an insertion rod with a threaded rod tip inserted through bore 305, through channels 189 and threaded into bore 292. Another portion of the insertion instrument may latch securely on to second end body 152. The spacer 100 may be inserted with first end 118 leading; leading edge 284 and smooth leading surface 280 may ease the insertion step. If necessary, force may be applied to the instrument and spacer 100 to facilitate insertion; boss 304 and second end body 152 are intended to withstand and transmit the insertion forces. As insertion commences, the spacer 100 is in the collapsed, compact or closed configuration seen in FIG. 1A and FIG. 8. Before insertion is complete, the expansion of the spacer 100 may begin.

Figure 2A:
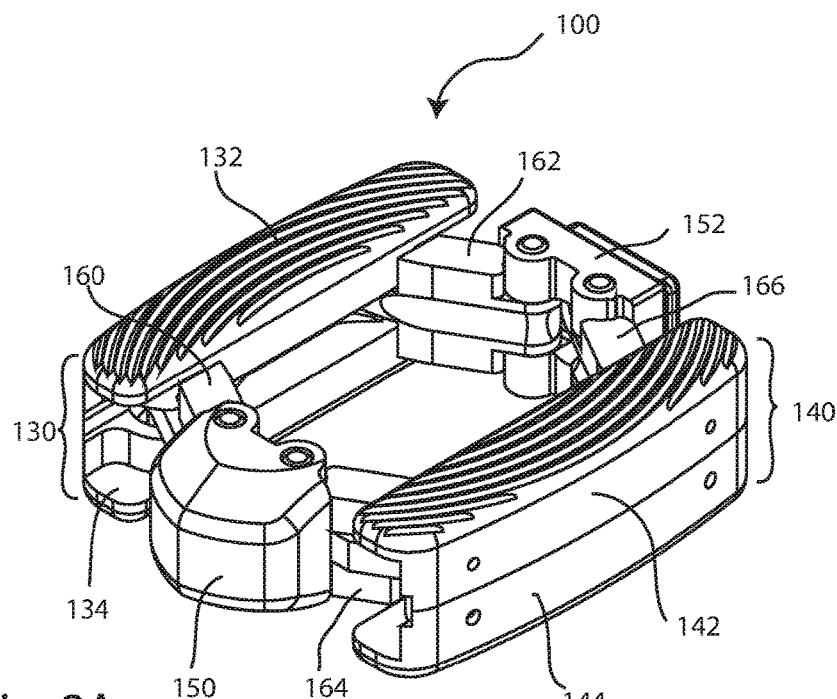
FIG. 2A is an isometric view of the interbody spacer of FIG. 1 in a partially expanded configuration in which the spacer is expanded horizontally.

After or during insertion between the vertebral bodies, the insertion instrument may be manipulated to urge horizontal expansion of the spacer 100, to attain the expanded configuration seen in FIG. 2A. For example, the rod member of an insertion instrument may be rotated or ratcheted to provide an axial force along axis 102 to urge first end body 150 and second end body 152 toward one another, decreasing the distance between them. The axial force urges joints 290 to pivot open, pushing first and second support members 130, 140 outward and away from one another along axis 104, into the horizontally expanded configuration seen in FIGS. 2A, 2B and 9. During this horizontal expansion, links 160, 162, 164, 166 pivot outward, or laterally relative to axis 102.

Figure 8:
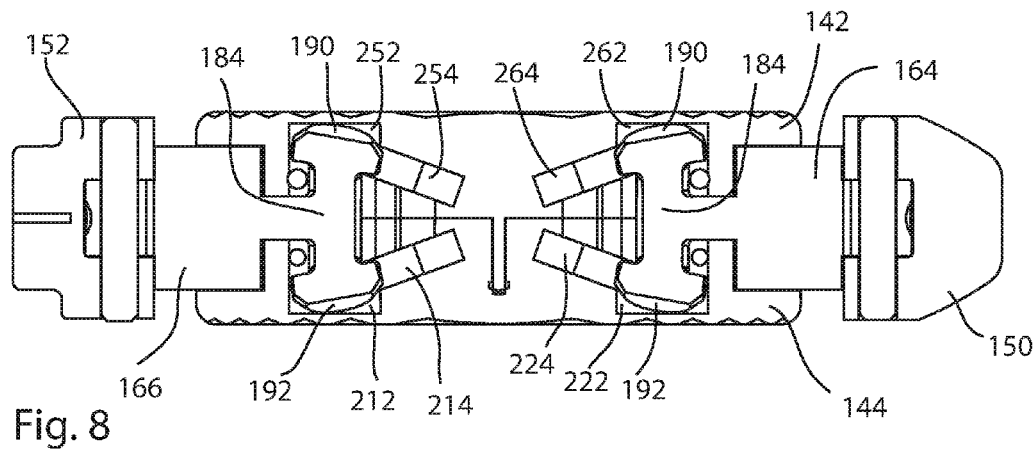
FIG. 8 is a side cross-sectional view of the spacer of FIG. 1 in the collapsed configuration.

FIG. 8 depicts the collapsed configuration. Spools 184 are received in the cylindrical portions 212, 222, 252, 262 of the first and second receptacles of the upper 142 and lower 144 bodies. The upper and lower ramped surfaces 190, 192 of the links are oriented such that the spools are prevented from moving into the ramped portions, or expansion slots, 214, 224, 254, 264. Vertical expansion cannot be achieved while the spacer 100 is in the collapsed configuration.

Figure 2B:
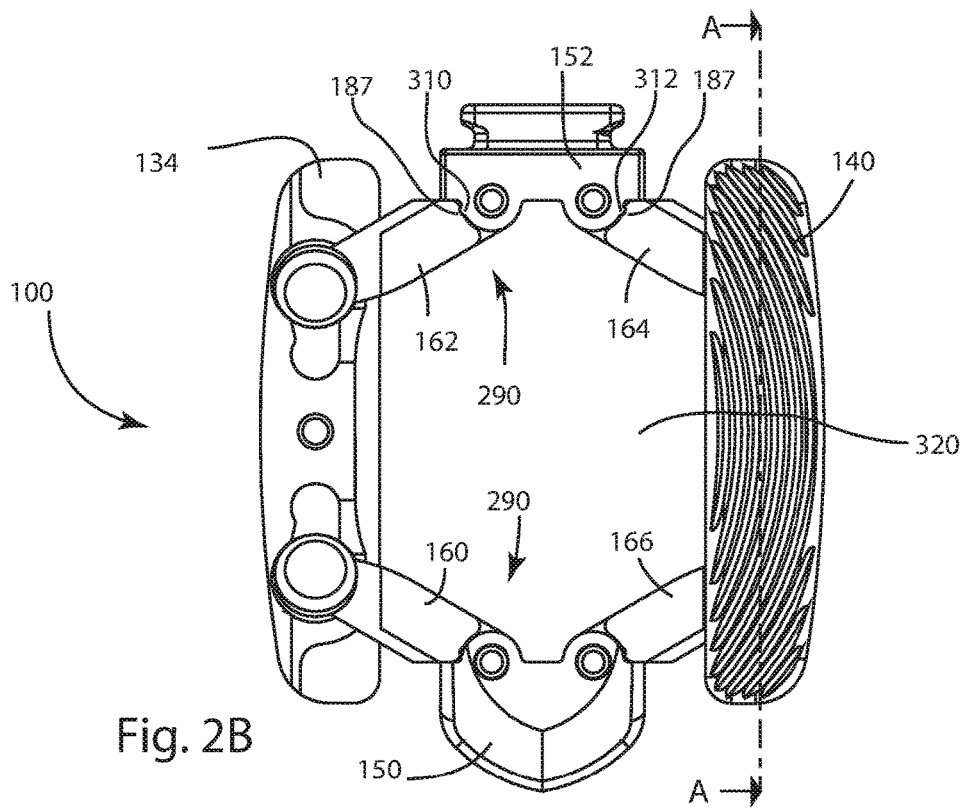
FIG. 2B is a top down view of the interbody spacer of FIG. 2A absent an upper body.
Figure 9:
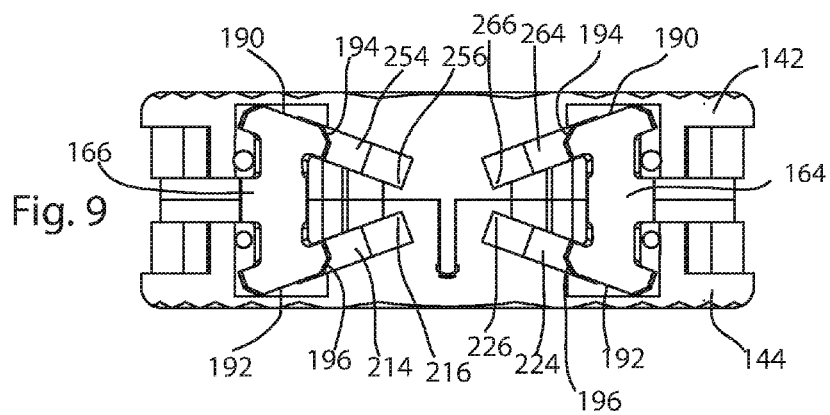
FIG. 9 is a side cross-sectional view of the spacer of FIG. 1 in the horizontally expanded configuration, taken along section line A-A in FIG. 2B.

FIG. 9 depicts the horizontally expanded configuration. Due to rotation of the joints, spools 184 have rotated to the point where the upper 190 and lower 192 ramped surfaces are now parallel with the expansion slots 214, 224, 254, 264. The angle of the upper ramped surface 190 of each spool matches the angle of the upper ramped surface of the expansion slot 254, 265 with which it is aligned. The angle of the lower ramped surface 192 of each spool matches the angle of the lower ramped surface of the expansion slot 214, 224 with which it is aligned. The chamfered guide surfaces 194, 194 may facilitate alignment of the upper and lower ramped surfaces with the expansion slots. With reference to FIG. 2B, locking features 310, 312 are received in locking recesses 187 to lock the spacer in the horizontally expanded configuration. The stop faces 294, 296, 314, 316 on the end bodies 150, 152 prevent overexpansion of the device. An inner chamber 320 is bounded by a horizontal perimeter formed by the support members 130, 140 and end bodies 150, 152 interspersed with links 160, 162, 164, 166.

Figure 3A:
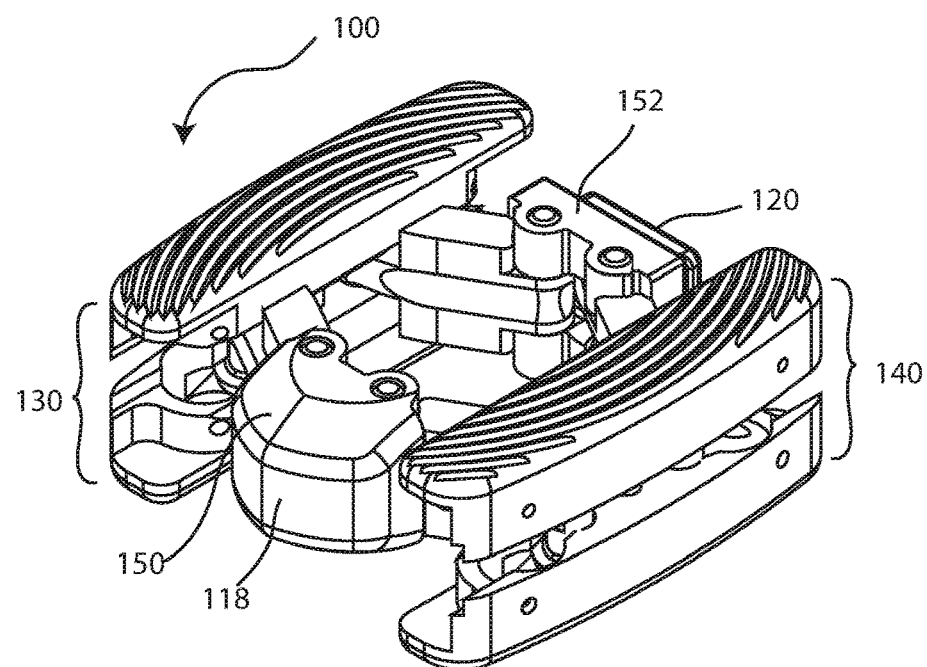
FIG. 3A is an isometric view of the interbody spacer of FIG. 1 in a fully expanded configuration in which the spacer is expanded horizontally and vertically.
Figure 3B:
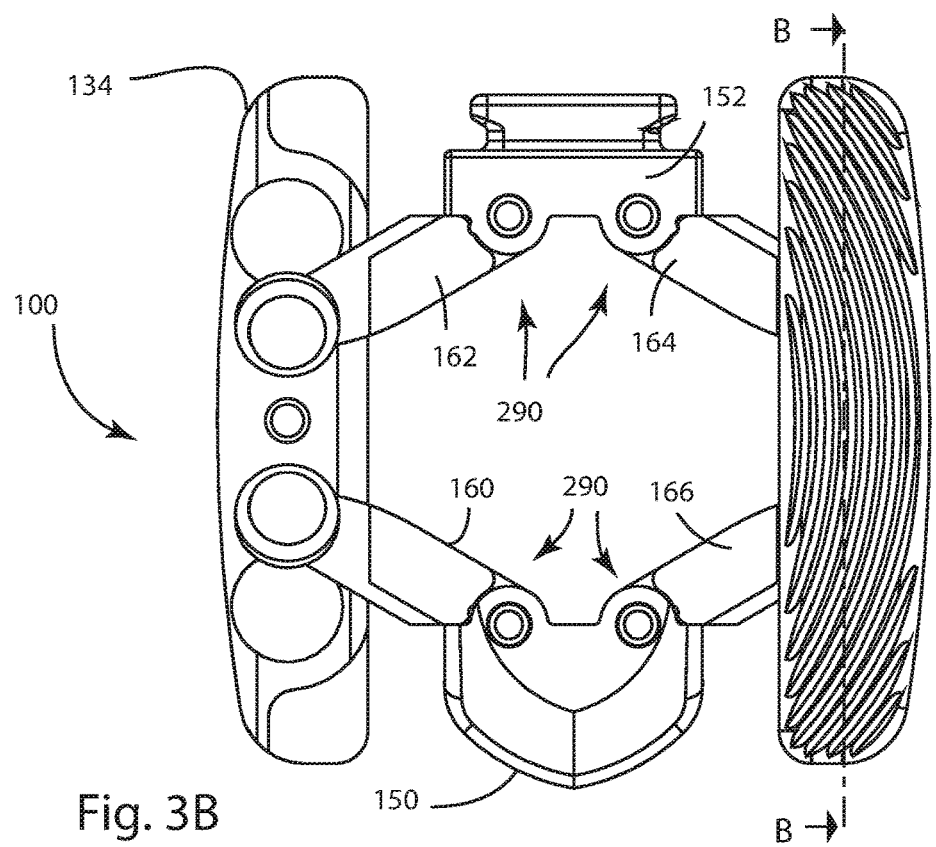
FIG. 3B is a top down view of the interbody spacer of FIG. 3A absent an upper body.
Figure 10:
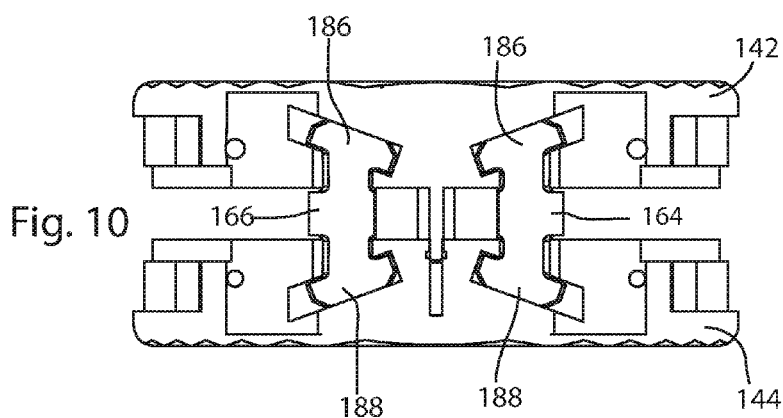
FIG. 10 is a side cross-sectional view of the spacer of FIG. 1 in the horizontally and vertically expanded configuration, taken along section line B-B in FIG. 3B.
Figure 11:
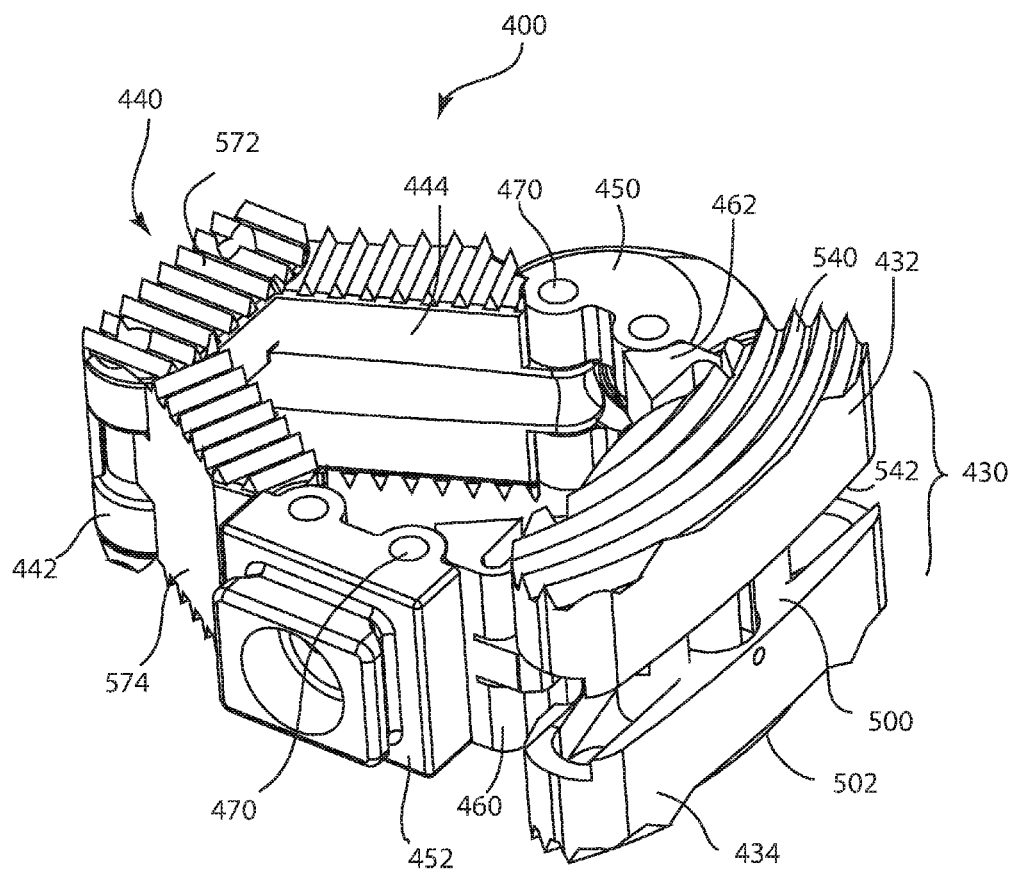
FIG. 11 is a isometric view of another embodiment of an interbody spacer in an expanded configuration.
Figure 12A:
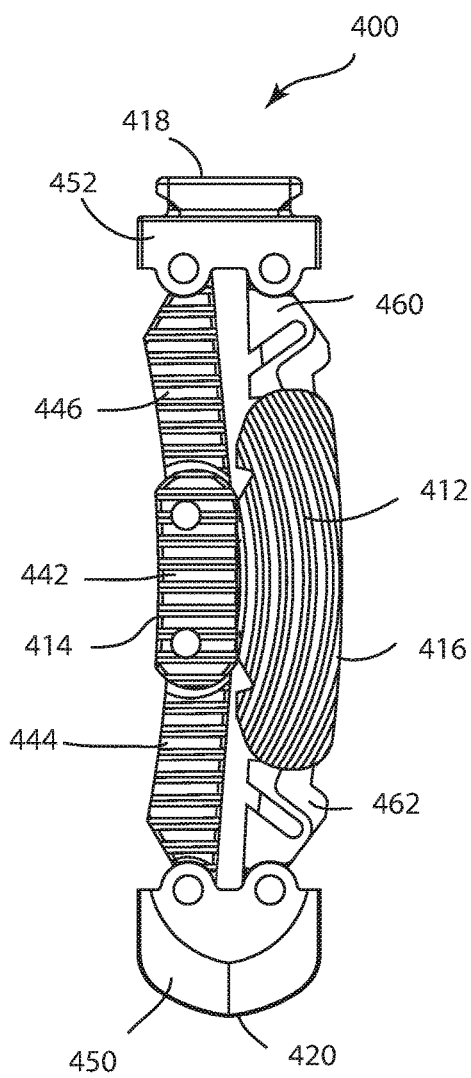
FIG. 12A is a top down view of the interbody spacer of FIG. 11 in a collapsed configuration.
Figure 12B:
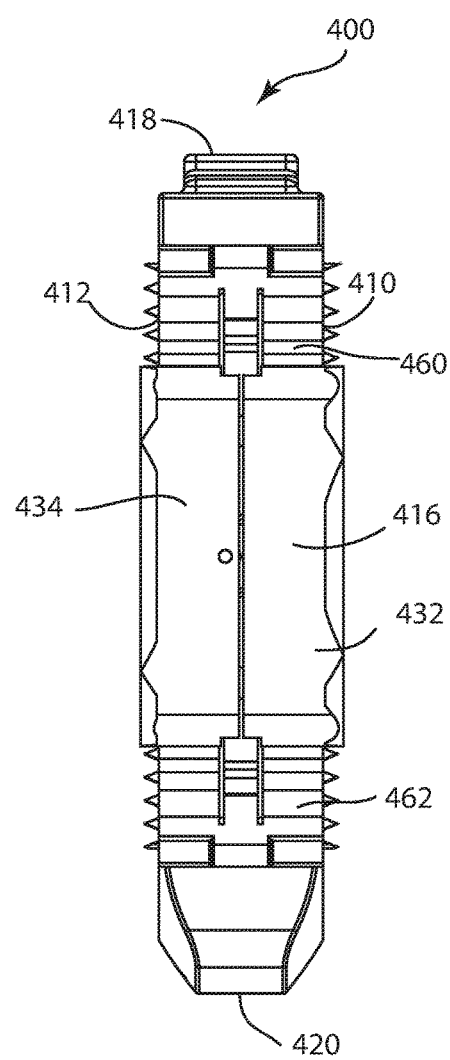
FIG. 12B is a side view of the interbody spacer of FIG. 11 in a collapsed configuration.

Further axial force along axis 102, which may be attained by further rotation of a rod portion of the insertion instrument, urges the spools 184 into the expansion slots, pushing the upper 132, 142 and lower 134, 144 bodies away from one another along axis 106, into the vertically expanded configuration seen in FIGS. 3A and 10. During vertical expansion, ramped surfaces 190 may slide against the upper ramped surfaces of the expansion slots 254, 264, and the ramped surfaces 192 may slide against the lower ramped surfaces of the expansion slots 214, 224. FIG. 10 depicts the horizontally and vertically expanded configuration of the spacer 100. Spools 184 have been urged toward one another within in each of the upper and lower bodies into the expansion slots 214, 224, 254, 264. The upper and lower head portions 186, 188 are received in the expansion slots, and into the undercuts 216, 226, 256, 266. Ramped surfaces 190 may be flush against the upper ramped surfaces of the expansion slots 254, 264, and the ramped surfaces 192 may be flush against the lower ramped surfaces of the expansion slots 214, 224. The height of the inner chamber 320 is increased with the vertical expansion, but the footprint or horizontal perimeter may remain constant. The inner boundaries of the expansion slots provide a physical stop to prevent any further vertical expansion.

In other embodiments of the disclosure, the spacer could be expanded on only one side; for example support member 130 could be horizontally and/or vertically expanded while support member 140 remains in its collapsed position, or vice versa. In another embodiment, a non-expanding support member such as 140 could be solid. This type of asymmetrical expansion could provide a lordotic or kyphotic correction.

An alternative embodiment of the disclosure is shown in FIGS. 11-15. Spacer 400 may be horizontally and/or vertically expanded to provide an asymmetric construct. As shown in FIGS. 13A and 13B, when fully expanded, spacer 400 may be asymmetric relative to at least lengthwise spacer axis 402. Horizontal expansion along first axis 404 in a first direction may be asymmetric relative to spacer axis 402 and second axis 406. Vertical expansion along axis 406 in a second direction may be asymmetric relative to spacer axis 402 and first axis 404. Like spacer 100, an expansion instrument may be deployed to provide an axial force along axis 402, through which horizontal (or lateral) expansion first occurs along axis 404, followed subsequently by vertical expansion along axis 406. The expansion along axis 404 may be asymmetrical in that one side of the spacer, relative to spacer axis 402, moves a greater distance than the opposite side of the spacer relative to spacer axis 402. Similarly, the expansion along axis 406 may be asymmetrical in that one side of the spacer, relative to spacer axis 402, moves a greater distance vertically than the opposite side of the spacer relative to spacer axis 402. The degree of vertical expansion may be less than, equal to, or greater than the degree of horizontal expansion. In an exemplary embodiment, the absolute distance of horizontal expansion may be greater than the absolute distance of vertical expansion.

Referring to FIGS. 12A, 12B, 13A and 13B, the spacer 400 includes an upper surface 410 and a lower surface 412 separated by a first side 414 and a second side 416. A first end 418 and a second end 420 are separated by the upper and lower surface and first and second sides.

Referring to FIGS. 11 through 15, the interbody spacer 400 comprises a set of bodies pivotably linked together, allowing the bodies to articulate relative to one another. A first support member 430 includes an upper body 432 and a lower body 434. A second support member 440 includes a side body 442 and first and second pivot bodies 444, 446. The pivot bodies 444, 446 may be mirror images of one another. A first end body 450 is pivotably linked to the first and second support members 430, 440 toward the first end 418, and a second end body 452 is pivotably linked to the first and second support members 430, 440 toward the second end 420. A first link 460 pivotably joins the second end body 452 to the first support member 430, and a second link 462 pivotably joins the first end body 450 to the first support member 430. The first and second links 460, 462 may be mirror images of one another. Similar to spacer 100, a plurality of pins 470 pivotably connect the first and second pivot bodies 444, 446 and the first and second links 460, 462 with the end bodies 450, 452.

Figure 14:
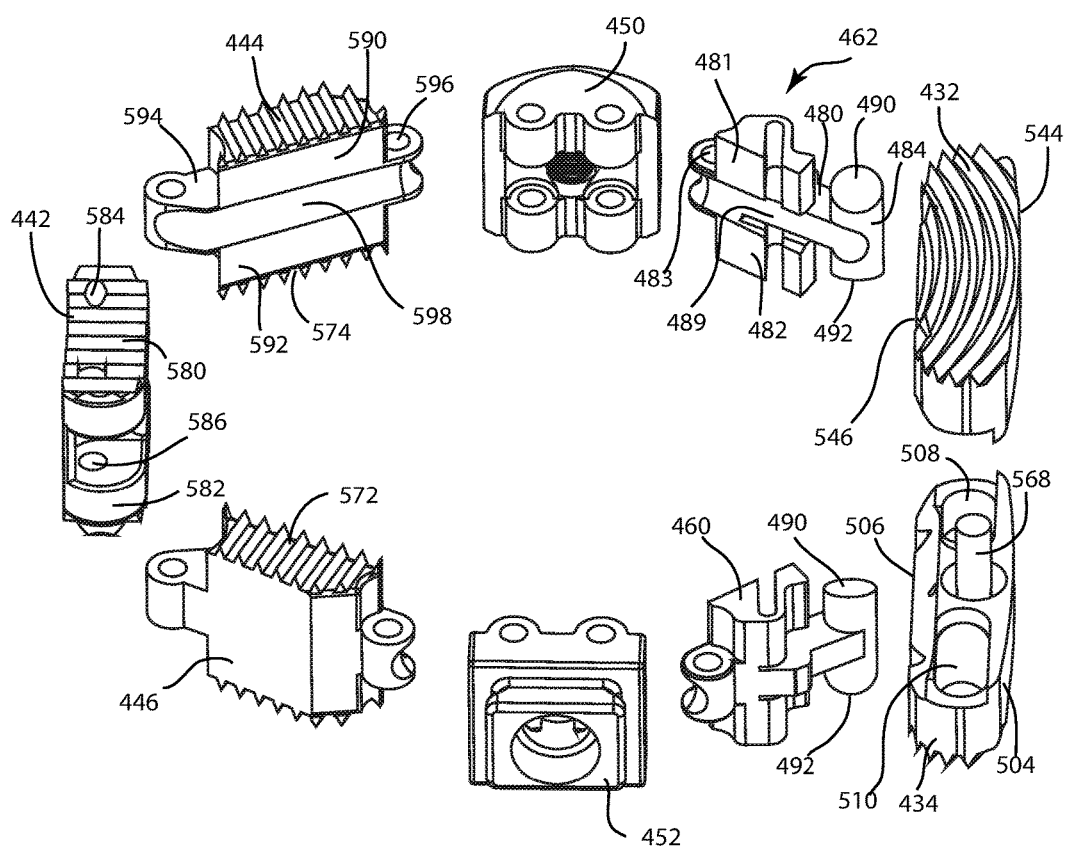
FIG. 14 is an isometric exploded view of the interbody spacer of FIG. 11.
Figure 15:
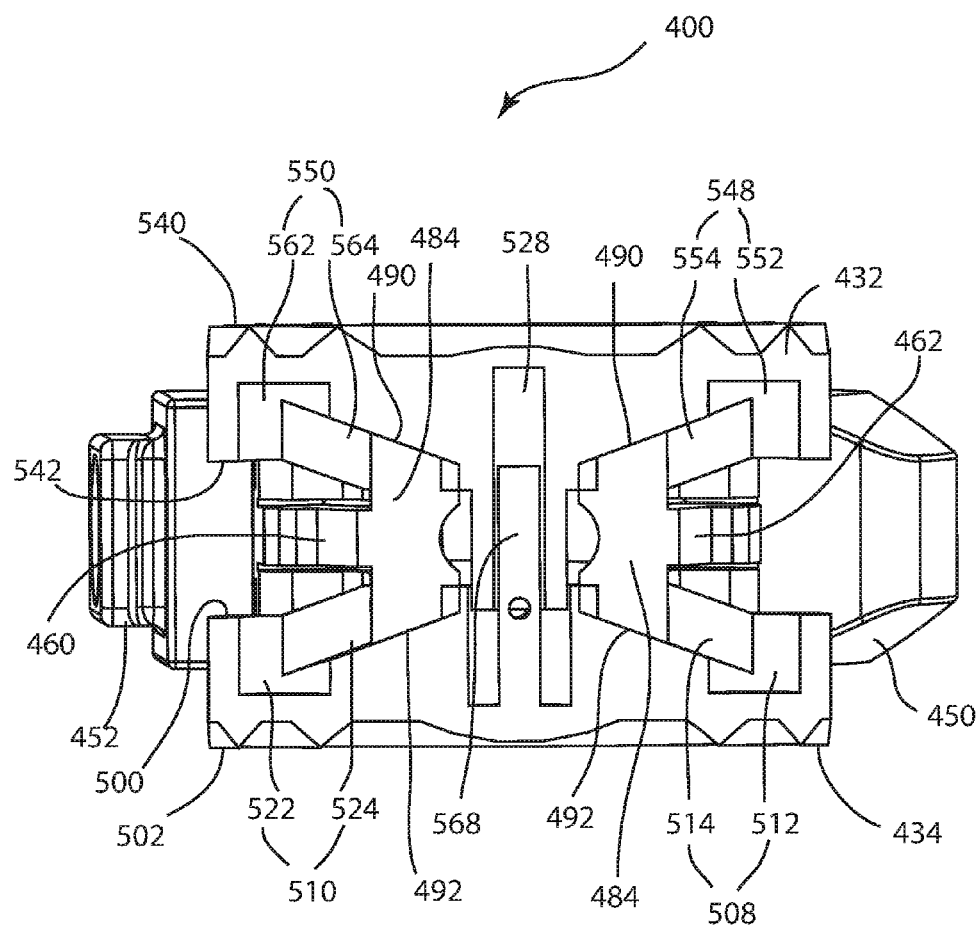
FIG. 15 is a side cross-sectional view of the spacer of FIG. 11 in the horizontally and vertically asymmetrically expanded configuration, taken along section line C-C in FIG. 13A.

Turning to FIGS. 14 and 15, additional detail of spacer 400 is shown. Link 462 is described in additional detail; it is understood that the description of link 462 applies to link 460, which is a mirror image. Link 462 includes a link body 480, which is aligned along a horizontal plane which may be parallel to spacer axis 402 when the spacer is properly assembled. An upper support block 481 is on an upper side of link body 480, opposite a lower support block 482 on the lower side of the link body. An open bore 483 is formed on link body 480 for rotatably receiving link 470. In some embodiments, a locking recess may be formed on the link body to facilitate locking with one of the end bodies, to prevent unintended movement out of the horizontally expanded configuration. A channel 489 may be recessed into the link body to provide passage for instrumentation and/or allograft or other materials. Opposite the open bore, a cylinder 484 includes an upper ramped surface 490, and a lower ramped surface 492. Upper and lower ramped surfaces 490, 492 are non-parallel with respect to each other. Each ramped surface 490, 492 may be angled in a range of 0° to 60° relative to the horizontal plane of the link body 480. In an exemplary embodiment, the ramped surfaces may be at an angle of 20° to the horizontal plane of the link body 480.

Support member 430 includes upper and lower bodies 432, 434. Referring to FIGS. 14 and 15, lower body 434 includes an upper face 500 and a lower face 502, separated by an outer face 504 and an inner face 506. Lower body 434 further includes a first receptacle 508 and a second receptacle 510. The first receptacle 508 includes a cylindrical portion 512 and a ramped portion 514 with a ramped lower surface. The second receptacle 510 may be a mirror image of the first receptacle, and includes a cylindrical portion 522, a ramped portion 524 with a ramped surface. Each ramped surface may be angled in a range of 0° to 60° relative to the horizontal plane of the lower body 434. In an exemplary embodiment, the ramped surfaces may be at an angle of 20° to the horizontal plane of the lower body 434. A peg 568 protrudes from the body 434 between the receptacles.

Upper body 432 includes an upper face 540 and a lower face 542, separated by an outer face 544 and an inner face 546. Depressed into the lower face 542 are a first receptacle 548 and a second receptacle 550. The first receptacle 548 includes a cylindrical portion 552 and a ramped portion 554 with a ramped upper surface. The ramped portion may also be referred to as an expansion slot. Each ramped surface may be angled in a range of 0° to 60° relative to the horizontal plane of the upper body 432. In an exemplary embodiment, the ramped surfaces may be at an angle of 20° to the horizontal plane of the upper body 432. The second receptacle 550 may be a mirror image of the first receptacle, and includes a cylindrical portion 562 and a ramped portion 564. A blind bore 528 extends into the body 434 between the receptacles. When the spacer 400 is properly assembled, peg 568 is received in blind bore 528 to provide proper alignment of upper and lower bodies, provide support in the collapsed configuration, and provide stability. Upper face 540 of upper body 432 and lower face 502 of lower body 434 may be exteriorly facing when the spacer 400 is properly implanted, and may include ridges, furrows, points, surface roughening, or other surface treatments to facilitate engagement with the adjacent vertebral bodies.

The appearance, shape, description and function of end body 150 may apply to end body 450. Similarly, the appearance, shape, description and function of end body 152 may apply to end body 452.

In the embodiment depicted in FIGS. 11-15, second support member 440 includes side body 442 and first and second pivot bodies 444, 446. In other embodiments of the invention, the second support member may comprise more or fewer connected bodies. Second support member includes an upper exterior surface 572 and a lower exterior surface 574. Side body 442 includes an upper support block 580 and a lower support block 582. Connection features 584, 586 are formed at opposite ends for connection with the pivot bodies. First pivot body 444 includes an upper support block 590 and a lower support block 592. Connection features 594, 596 are formed at opposite ends for connection with the side body 442 and end body 450. A channel 598 may be recessed into the pivot body to provide passage for instrumentation and/or allograft or other materials. When the spacer 400 is properly assembled, the connection features of the pivot bodies may fit together with the connection features of the side body to provide essentially continuous unbroken upper and lower exterior surfaces 572, 574 whether the spacer is in a compact or an expanded configuration. The upper and lower surfaces 572, 574 may be essentially parallel to one another, and parallel to horizontal axis 404; in alternate embodiments they may be non-parallel. Similar to the first support member 430, the upper and lower exterior surfaces of the second support 440 member may include ridges, furrows, points, surface roughening, or other surface treatments to facilitate engagement with the adjacent vertebral bodies.

Spacer 400 is expandable in the same manner as spacer 100, and the description of expansion of spacer 100 applies to spacer 400. A single axial force along axis 402 may expand the spacer first horizontally and then vertically. During horizontal, or lateral, expansion, first end body 450 is drawn toward second end body 452, which urges side body 442 and first support member 430 and to move away from one another and perpendicularly away from spacer axis 402. This horizontal expansion is asymmetrical, as side body 442 moves a greater distance away from spacer axis 402 than does first support member 430, as is clearly shown in FIG. 13A. An inner chamber 520 is bounded by a horizontal perimeter formed by the support members 430, 440, end bodies 450, 452 and links 460, 462. During horizontal or lateral expansion, cylinders 484 of links 460, 462 pivot so that at the furthest extent of horizontal expansion, the ramped surfaces 490, 492 of the links are aligned with the upper and lower ramped surfaces of the receptacles 548, 550, permitting vertical expansion to commence. During the vertical expansion, lower body 432 is urged away from upper body 434, resulting in an asymmetrically expanded configuration in which the first side 414 and first support member 430 of the spacer 400 is taller than the second side 416 and second support member 440 relative to the first axis 404, as is clearly shown in FIG. 13B. The asymmetrical vertical expansion may be used to provide a lordotic, kyphotic, scoliotic or other type of vertebral height correction.

FIGS. 16A-24B illustrate another embodiment of an intervertebral spacer which may be horizontally and vertically expanded. Interbody spacer 600, which may also be referred to as a device, cage or implant, is expandable from the collapsed, or compact configuration seen in FIG. 16A, along a first axis and a second axis. The spacer 600 has a longitudinal spacer axis 602, and may be expandable in a first direction along a first axis 604 which may be a horizontal or lateral expansion axis, to a horizontally expanded configuration seen in FIG. 16B. The device may be further expanded in a second direction along a second axis 606, which may be a vertical expansion axis, to the horizontally and vertically expanded configuration seen in FIG. 16C. Axes 604, 606 may be perpendicular to each other and perpendicular to spacer axis 602. When implanted between two vertebral bodies in a portion of a spine, the spacer 600 is expandable laterally along the first axis 604, and vertically, or cephalad-caudally, along the second axis 606. A single axial force acting along the spacer axis 602 may provide the expansion force for both the horizontal and vertical expansion. The spacer 600 may be bilaterally symmetrical with respect to a vertical plane extending along spacer axis 602, and may be bilaterally symmetrical with respect to a horizontal plane extending along spacer axis 602.

Referring to FIGS. 16A-16C, the spacer 600 includes an upper surface 610 and a lower surface 612 separated by a first side 614 and a second side 616. A first or nose end 618 and a second or back end 620 are separated by the upper and lower surface and first and second sides. The interbody spacer 600 comprises a set of bodies pivotably linked together, allowing the bodies to articulate relative to one another. A first support member 630 includes a first upper body 632 and a first lower body 634. A second support member 640 includes a second upper body 642 and a second lower body 644. A first end body, or nose 650 is pivotably linked to the first and second support members 630, 640 toward the first end 618, and a second end body or rear body 652 is pivotably linked to the first and second support members 630, 640 toward the second end 620. The upper and lower bodies may be mirror images of one another, as may the first and second support members. As seen in FIG. 16C, a locking screw 654 prevents unintentional movement of the spacer 600 from the laterally and vertically expanded configuration. The locking screw 654 may provide supplementary or final locking of the spacer.

Figure 17:
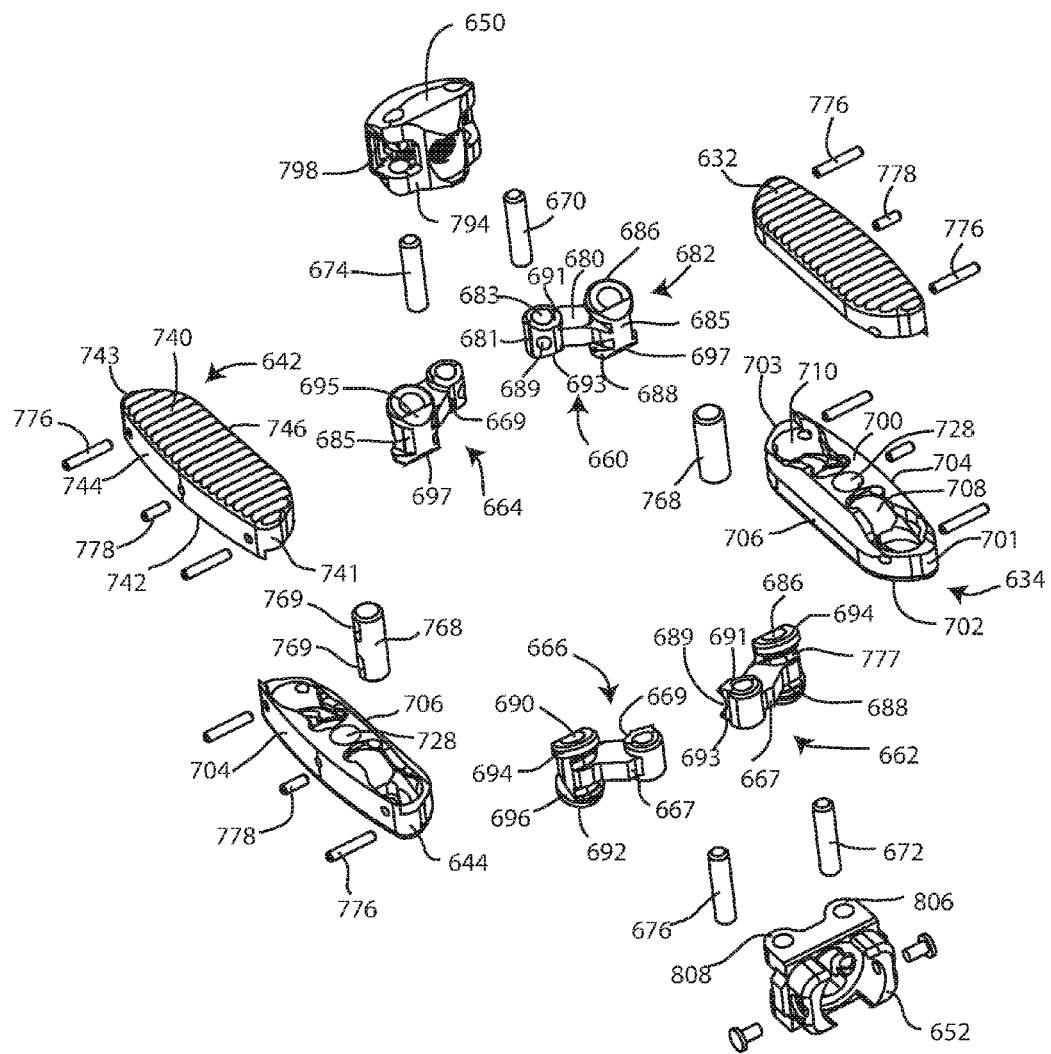
FIG. 17 is an isometric exploded view of the interbody spacer of FIG. 16A.
Figure 18A:
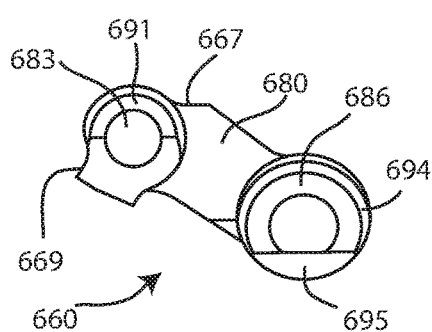
FIG. 18A is a top down view of a link body of the interbody spacer of FIG. 16A.
Figure 18B:
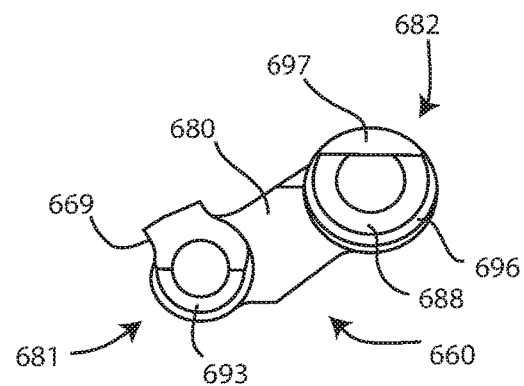
FIG. 18B is a bottom up view of the link body of FIG. 18A.
Figure 18C:
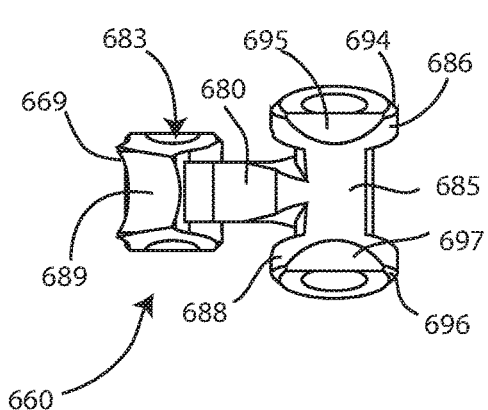
FIG. 18C is a side view of the link body of FIG. 18A.
Figure 18D:
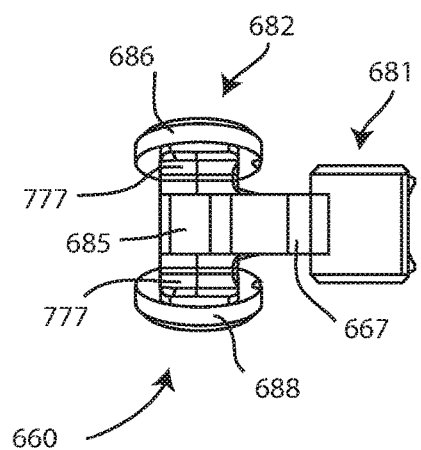
FIG. 18D is an opposite side view of the link body of FIG. 18C.

Referring to FIG. 17, additional components of the spacer 600 may be seen. A plurality of links 660, 662, 664, 666 link the support members 630, 640 to the end bodies 650, 652. Link 660 joins first end body 618 to upper and lower bodies 632, 634, via a pin 670. Link 662 joins second end body 620 to the opposite ends of upper and lower bodies 632, 634, via a pin 672. Similarly, link 664 joins first end body 618 to upper and lower bodies 642, 644, via a pin 674. Link 666 joins second end body 620 to the opposite ends of upper and lower bodies 642, 644 via a pin 676.

Each link 660, 662, 664, 666 includes a pivot member which is generally shaped as a spool, in the embodiment depicted. The pivot members may alternately take on other shapes such as cylinders with sloped ends or two generally spherical ends connected by a post. Link 660 is described herein in further detail, but it is appreciated that the description also applies to the other links 662, 664, 666. Link 660 includes a link body 680, which is aligned along a horizontal plane which may be parallel to spacer axis 602 when the spacer is properly assembled. Link body 680 extends between and connects a link first end 681 to a link second end 682. An open bore 683 is formed in the link first end 681 for rotatably receiving pin 670. Beveled surfaces 691, 693 may be formed on opposite faces of the link first end 681. A first stop surface 667 is formed on the link body which meets with a stop surface on one of the end bodies during spacer expansion, to limit lateral expansion of the spacer 600 and prevent over-expansion. A second stop surface 669 is formed on the link body which meets with a stop surface on one of the end bodies in the fully collapsed configuration. A concave channel 689 may be recessed into the link to provide passage for instrumentation and/or allograft or other materials. In other spacer embodiments, one or more links may be free of stop surfaces.

Opposite the link first end 681, the spool-shaped link second end 682 comprises a stem portion 685 which supports an upper head 686 and a lower head 688. In the embodiment shown, the stem portion 685 is non-circular; the faceted or squared-off shape of the stem between the heads prevents additional axial rotation of the second end 682 once the spacer 600 is in the laterally expanded configuration. Upper head 686 includes an upper ramped surface 690, and lower head 688 includes a lower ramped surface 692. Upper and lower ramped surfaces 690, 692 are non-parallel with respect to each other. Each ramped surface 690, 692 may be angled in a range of 0° to 60° relative to the horizontal plane of the link body 680 between the first and second ends. In an exemplary embodiment, the ramped surfaces may be at an angle of 20° to the horizontal plane of the link body 680. Each head 686, 688 may be of a larger diameter than the stem 685. A chamfer 694 may encircle the upper head 686 adjacent the ramped surface 690; similarly a chamfer 696 may encircle the lower head 688 adjacent the ramped surface 692. The link first end 681 may include similar chamfers. The chamfers 694, 696 may act as guide surfaces as the spacer 600 transitions from horizontal expansion to vertical expansion. In addition to the chamfer, a bevel 695 may be formed on upper head 686, and a corresponding bevel 697 may be formed on lower head 688; other embodiments may lack the bevels.

With reference to FIGS. 17, and 19A-D, support member 630 includes upper and lower bodies 632, 634. First lower body 634 is described herein in further detail, but it is appreciated that the description may also apply to the second lower body 644, and also upper bodies 632, 642, as all four bodies may be identical in an embodiment except for their positional arrangement with each other and other spacer elements. Each upper and lower body is generally elongated between a first end 701 and a second end 703, and has generally rounded perimeters and edges. Lower body 634 includes an upper face 700 and a lower face 702, separated by an outer face 704 and an inner face 706. Depressed into the upper face 700 are a first receptacle 708 and a second receptacle 710. The first receptacle 708 includes a first recessed portion 712 which includes a flat lower surface 713 and a second recessed portion 714 with a ramped lower surface 715. A first constriction 709 may be formed in the upper face 700 between the first and second recessed portions 712, 714 of the first receptacle. An undercut 716 is formed in the perimeter of the receptacle 708. A ramp 717 occupies a portion of the first recessed portion 712 and extends toward the second recessed portion 714. A retention feature 718, which in the embodiment shown is a raised lip, is positioned between the first and second recessed portions 712, 714, creating a pocket around the second recessed portion 714.

The second receptacle 710 may be a mirror image of the first receptacle, and includes a first recessed portion 722 which includes a flat lower surface 723 and a second recessed portion 724 with a ramped lower surface 725; the receptacle 710 further includes an undercut 726 and a retention feature 728. A second constriction 711 may be formed in upper face 700 between the first and second recessed portions 722, 724 of the second receptacle 710. A ramp 727 occupies a portion of the first recessed portion 722 and slopes toward the second recessed portion 724. Each ramp may be angled in a range of 0° to 60° with respect to the horizontal plane of the lower body 634. In an exemplary embodiment, the ramps may be at an angle of 20° with respect to the horizontal plane of the lower body 634. A blind bore 728 extends into the body 634 between the receptacles. The first recessed portions 712, 722 extend deeper within the support body than do the second recessed portions 714, 724.

Figure 22A:
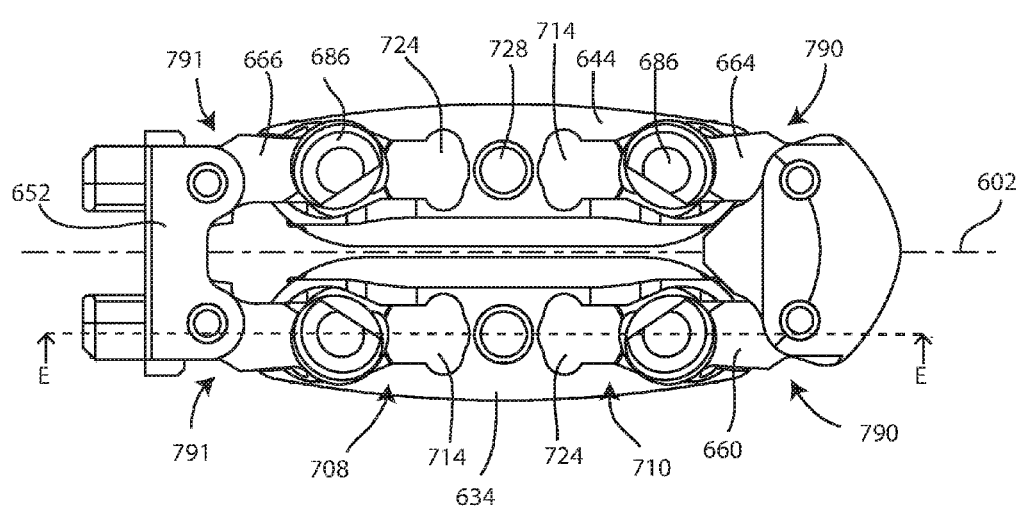
FIG. 22A is a top down partial view of the interbody spacer of FIG. 16A, with two upper support bodies absent to show the assemblage of the end bodies, links, and lower support bodies.

When the spacer 600 is in the collapsed and laterally expanded configurations as in FIGS. 21A and 22A, a link second end 682 is received in the first recessed portion 712. After vertical expansion as in FIG. 23A, the link second end 682 is received in the second recessed portion 714. The retention feature 718 can serve as a provisional locking structure, by prohibiting movement of the link second end from the second recessed portion 714 back to the first recessed portion 712, thus preventing unintentional vertical collapse of the spacer 600 before insertion of the locking screw 654 or other locking member.

First upper body 632 is described herein in further detail, but it is appreciated that the description also applies to the second upper body 642, which may be a mirror image of upper body 632. Referring to FIGS. 17 and 19D, upper body 632 extends between a first end 741 and a second end 743, and includes an upper face 740 and a lower face 742, separated by an outer face 744 and an inner face 746. Depressed into the lower face 742 is a first receptacle 748 and a second receptacle 750. The first receptacle 748 includes a first recessed portion 752 having a flat upper surface 753 and a second recessed portion 754 with a ramped upper surface 755. The second recessed portion may also be referred to as an expansion slot. An undercut 756 is formed in the second recessed portion 754 away from the first recessed portion and toward the center of the upper body. A ramp 757 occupies a portion of the first recessed portion 752 and slopes toward the second recessed portion 754. A retention feature 758 is positioned between the first and second recessed portions 752, 754, creating a pocket around the second recessed portion 754. Each ramp surface may be angled in a range of 0° to 60° with respect to the horizontal plane of the upper body 632. In an exemplary embodiment, the ramped surfaces may be at an angle of 20° with respect to the horizontal plane of the upper body 632. The second receptacle 750 may be a mirror image of the first receptacle, and includes a first recessed portion 762 having a flat surface 763, a second recessed portion 764 having a ramped surface 765, and an undercut 766. A ramp 767 occupies a portion of the first recessed portion 762 and slopes toward the second recessed portion 764. A retention feature 778 is positioned between the first and second recessed portions 762, 764, and a blind bore 771 is recessed into the lower surface 742.

In one or more embodiments, additional or alternate retention features may be included to provide locking which prevents movement of the link second end back from the second recessed portion back toward the first recessed portion. In an embodiment, at least one link head 686, 688 may include a raised bump, and at least one second recessed portion 714, 724, 754, 764 may include an indentation in its respective upper or lower surface. When vertical expansion is achieved, the bump is received in the indentation, providing provisional locking. In an embodiment, the locations of the bumps and indentations may be reversed. In another embodiment, a detent feature may project between one of more of the links and one or more of the upper and lower bodies to provide provisional locking. In another embodiment, a detent feature may project between one of more of the end bodies and one or more of the upper and lower bodies to provide provisional locking. In another embodiment, at least one of the upper and lower support bodies may include a flat segment at the end of the ramp 717, 727, 757, 767 toward the second recessed portion; in the vertically expanded configuration the link second ends would rest upon the flat segment after moving from the first recessed portion to the second recessed portion.

When the spacer 600 is properly assembled, a peg 768 is received in the blind bores 728, 771 of first lower body 634 and first upper body 632 and similarly second bodies 642, 644 to provide proper alignment of the upper and lower bodies, provide support in the collapsed configuration, and provide stability. Recesses 752, 762 in the lower face 742 on opposite ends of the upper body 632 receive portions of links 660, 662 when the implant is in the collapsed configuration as in FIG. 16A. A plurality of assembly pins 776 extend between the inner and outer faces of the lower and upper bodies and cooperate with undercuts 777 in the links to secure the spacer assemblage while permitting spacer expansion. Each peg 768 may be further secured to its respective lower and upper bodies by one or more capture pins 778, which extend through the respective body and into an elongated slot 769 on the peg 768 to retain the peg 768 in the blind bore 728 or 771, while permitting vertical expansion. In this or another embodiment, one or more detent features could project into the blind bore 728 or 771 after vertical expansion, to prevent unintentional collapse of the spacer.

Upper face 740 of upper body 632, and lower face 702 of lower body 634 may be exteriorly facing when the spacer 600 is properly implanted, and may include ridges, furrows, teeth, points, surface roughening, or other surface treatments to facilitate engagement with the adjacent vertebral bodies. In an alternate embodiment the first and second support members 630 and 640 may be of differing length, proportion and/or configuration, and one of the members may not expand vertically in order to provide asymmetric vertical expansion.

Referring to FIGS. 20A-20E, first end body 650 includes an outer or leading side 780 and an inner side 782. In the embodiment shown, the leading side 780 is smooth and bullet-nosed to facilitate insertion into the intervertebral space. A first niche 783 and a second niche 784, each sized to receive a portion of a link, are on opposite ends of the end body 650, opening toward the inner side 782. The end body 650 includes connection features 786, 788 for connection to links 660, 664 via pins 670, 674 to form two rotatable end joints 790. It is appreciated that other connection features and/or joint types could be used to achieve the same result within the scope of the invention. In the embodiment shown, each end joint 790 may rotate open up to 60°. In other embodiments, the end joints may rotate in a range from 20° to 100°. A threaded bore 795 extends through the first end body 750 to provide connection with insertion and/or deployment instrumentation. The threaded bore 795 may be perpendicular to the rotation axes of the connection features 786, 788. A pair of first stop faces 792, 794 meet with link stop faces 669 when the spacer 600 is collapsed. A pair of second stop faces 796, 798 prevent over-expansion of device 600 by directly abutting with opposing stop surfaces 667 on links 660, 664 when the device is in the laterally expanded and vertically expanded configurations.

Figure 24A:
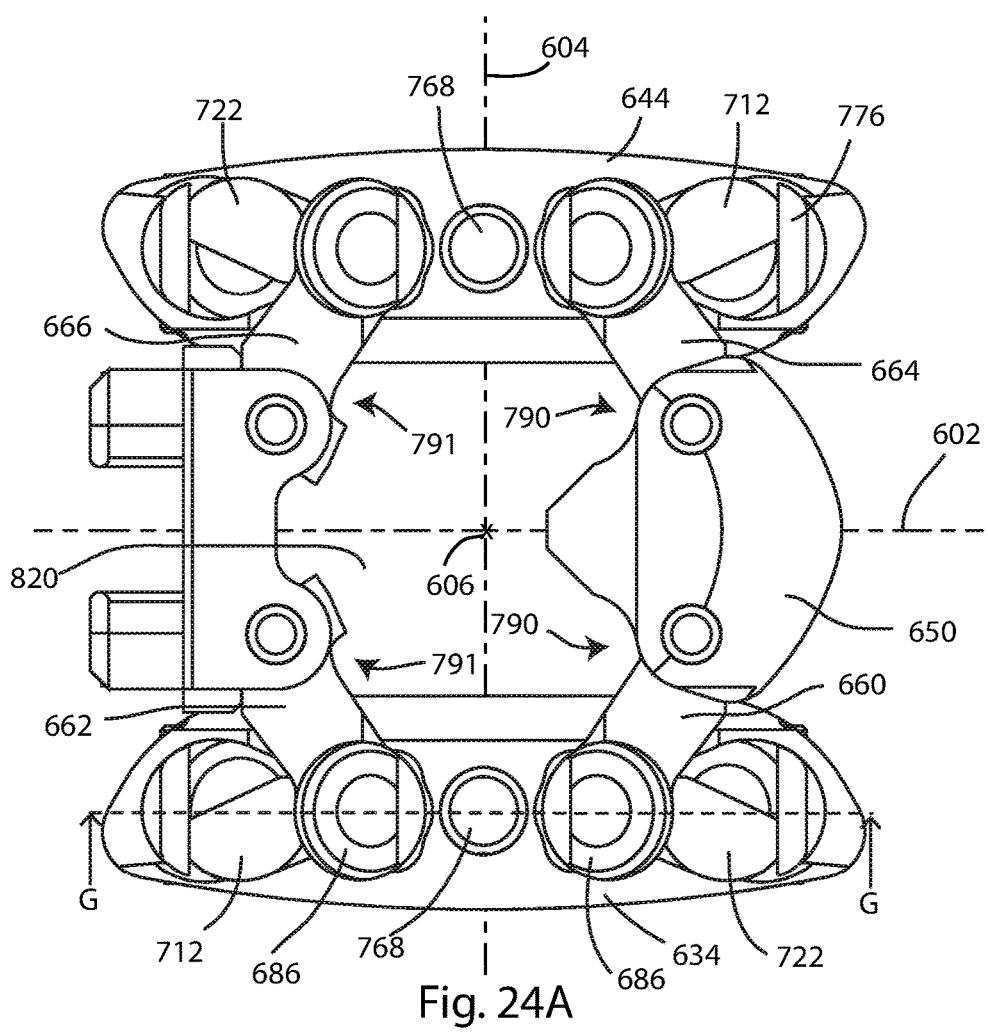
FIG. 24A is a top down partial view of the interbody spacer of FIG. 16C, with two upper support bodies absent to show the assemblage of the end bodies, links, and lower support bodies.

The second end body 752, which may be referred to as a back end or a rear end, includes an outer side 800 and an inner side 802. The exterior side 800 may include a protruding boss 804, which may facilitate engagement with instrumentation. A bore 805 extends through the second end body 852 between and in communication with the exterior face 800 and the inner side 802. The bore 805 may be non-threaded and non-circular and may allow access for instrumentation, graft insertion and locking screw 654. Other connection features including but not limited to posts, pins, depressions or additional bores may be present on the second end body for engagement with instrumentation. The non-circular bore 805 shape see in FIGS. 20A and 20B may allow an opening sized to accept large graft pieces, but still provides points of opposing contact with a shoulder 655 of the locking screw 654. In other embodiments, the bore 805 may be threaded or include other features for engagement with instrumentation. As seen in FIGS. 17 and 24A, the inner side 802 includes connection features 806, 808 for connection to links 662, 666 via pins 672, 676 to form rotatable end joints 791. The bore 805 may be perpendicular to the rotation axes of the connection features 806, 808. The second end body 752 includes first and second stop surfaces. When in the collapsed configuration, the first stop surfaces 810, 812 meet link stop surfaces 669. When laterally expanded, the second stop surfaces 814, 816 abut link stop surfaces 667, preventing unintentional excess lateral expansion of the space. It is appreciated that other stop features could also be included on first or second end bodies 650, 652, or that other types of tabs, latches, inserts, set screws, or locking features could be included on the device to keep the device rigidly locked open and prevent unintentional collapse.

The locking screw 654 includes a threaded portion 653 and a shoulder 655. The threaded portion 653 may be inserted longitudinally along axis 602 through rear bore 805, through chamber 820 and toward nose bore 795. The threaded portion may engage in nose bore 795, and screw shoulder 655 may abut the opening of rear bore 805 to rigidly lock the configuration of the spacer.

In a method of use, a patient may be prepared by performing a discectomy between two target intervertebral bodies. A transforaminal, posterior, lateral or anterior approach may be used. The vertebral bodies may be distracted, and spacer 600 mounted on an appropriate insertion instrument and inserted into the prepared space in between the vertebral bodies. In one example of the method, the spacer 600 is mounted onto an insertion rod having a threaded rod tip which is inserted through bore 805, and threaded into bore 795. Another portion of the insertion instrument may latch securely on to second end body 652. The spacer 600 may be inserted between the vertebral bodies with first end 618 leading; smooth leading surface 780 may ease the insertion step. If necessary, force may be applied to the instrument and spacer 600 to facilitate insertion; boss 804 and second end body 852 are intended to withstand and transmit the insertion forces. As insertion commences, the spacer 600 is in the collapsed, compact or closed configuration seen in FIG. 16A and FIG. 22A. Before insertion between the vertebral bodies is complete, the expansion of the spacer 600 may begin.

After or during insertion between the vertebral bodies, the insertion instrument may provide the impetus to urge horizontal or lateral expansion of the spacer 600, to attain the expanded configuration seen in FIG. 16B. For example, the rod member of an insertion instrument may be rotated or ratcheted to provide an axial force along axis 602 to urge first end body 650 and second end body 652 toward one another, decreasing the distance between them. The axial force urges joints 790, 791 to rotate open, pushing first and second support members 630, 640 outward and away from one another along axis 604, into the laterally expanded configuration seen in FIGS. 16B and 23A. During this horizontal expansion, links 660, 662, 664, 666 pivot outward, or laterally relative to axis 602.

Figure 22B:
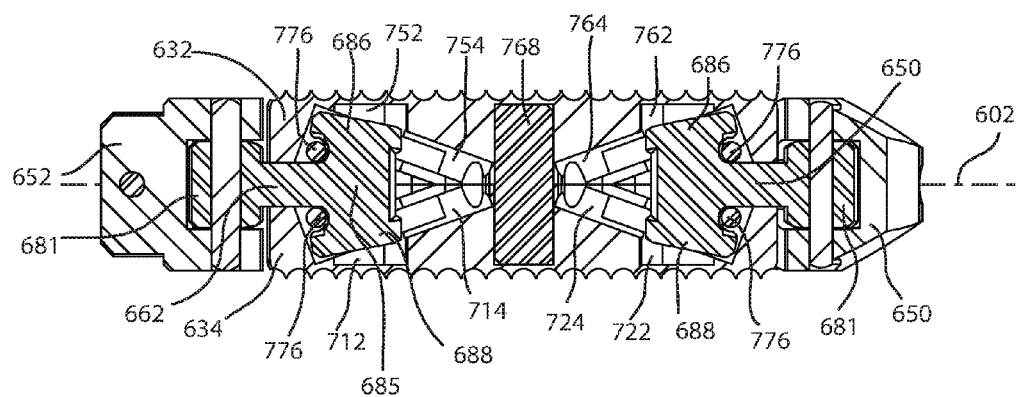
FIG. 22B is a cross-sectional view of the interbody space of FIG. 16A, taken along line E-E in FIG. 22A.

FIGS. 16A, 22A and 22B depict the collapsed configuration of spacer 600. Link second ends 682 are received in the first recessed portions 712, 722, 752, 762 of the first and second receptacles of the upper 632 and lower 634 bodies. In this position, the juxtaposition and shape of the stem portion 685 of each link relative to the expansion slots 714, 724, 754, 764 prevent movement of the links into the expansion slots. Thus, in the embodiment shown, vertical expansion cannot be achieved while the spacer 600 is in the collapsed configuration.

Figure 23A:
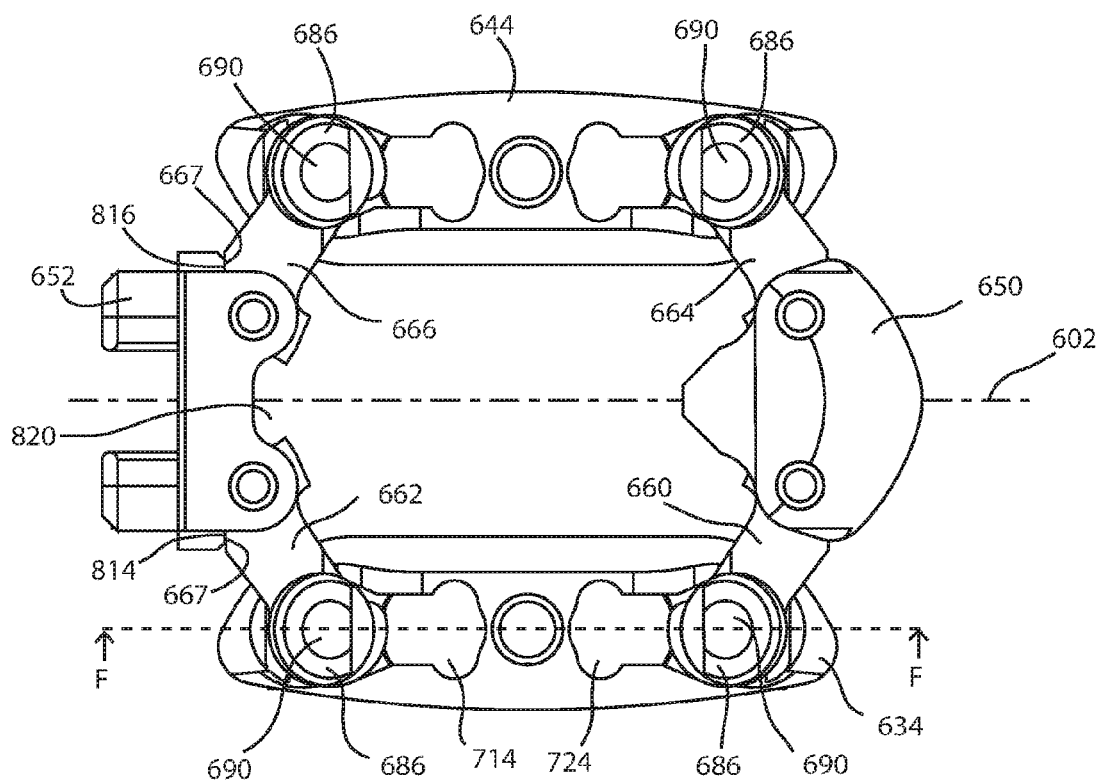
FIG. 23A is a top down partial view of the interbody spacer of FIG. 16B, with two upper support bodies absent to show the assemblage of the end bodies, links, and lower support bodies.
Figure 23B:
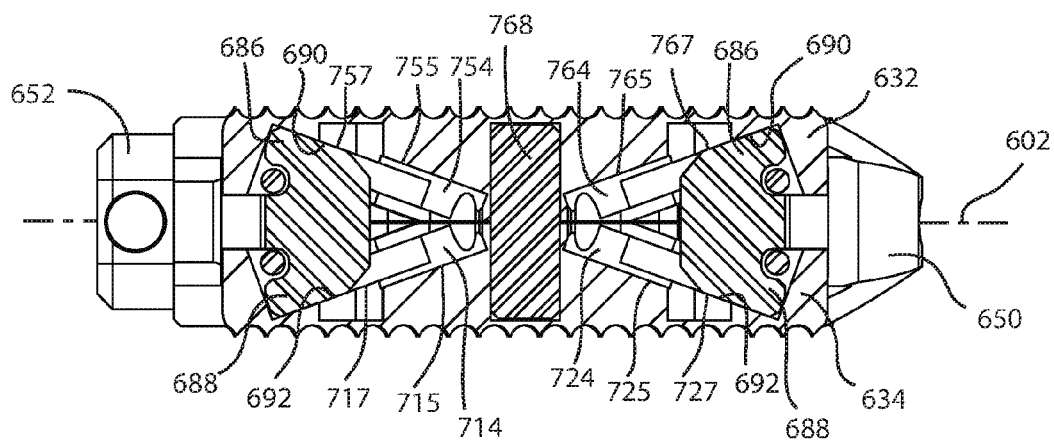
FIG. 23B is a cross-sectional view of the interbody space of FIG. 16B, taken along line F-F in FIG. 23A.

FIGS. 16B, 23A and 23B depict the laterally expanded configuration of spacer 600. Due to rotation of the joints 790 and 791, link second ends 682 have rotated within first recessed portions 712, 752 and 722, 762 to the point where the upper 690 and lower 692 ramped surfaces are now parallel with and rest against the ramps 717, 727, 757, 767. The angle of the upper ramped surface 690 of each link second end matches the angle of the upper ramped surface 755, 765 of the expansion slot 754, 764 with which it is now aligned. The angle of the lower ramped surface 692 of each link second end matches the angle of the lower ramped surface 715, 725 of the expansion slot 714, 724 with which it is now aligned. The chamfered guide surfaces 694 and bevels 691, 693, 695, 697 may facilitate alignment of the upper and lower ramped surfaces with the expansion slots. Interaction of the stop surface 667 on each respective link with the stop surfaces 796, 798 on the first end body 650, and with the stop surfaces 814, 816 on the second end body 652 prevents overexpansion of the device. An inner chamber 820 is bounded by a horizontal perimeter formed by the support members 630, 640 and end bodies 650, 652 interspersed with links 660, 662, 664, 666.

Figure 24B:
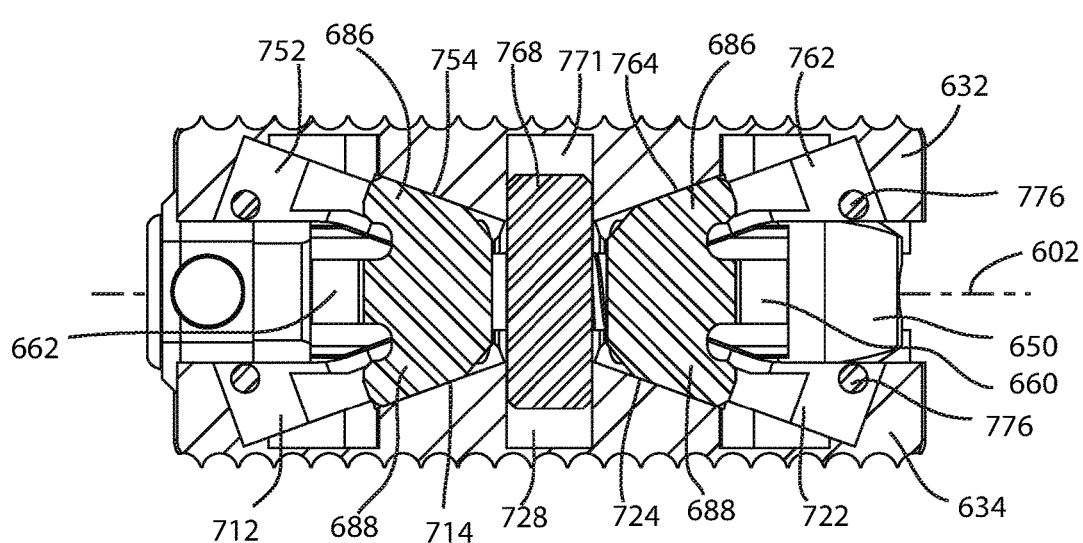
FIG. 24B is a cross-sectional view of the interbody space of FIG. 16C, taken along line G-G in FIG. 23A.

Upon further axial force along axis 602, which may be attained by further rotation of a rod portion of an insertion instrument, link second ends 682 of links 660, 662, 664, 666 cease rotation and are urged to move into the expansion slots 714, 754 and 724, 764 of each of the upper and lower bodies, thus pushing the upper 632, 642 and lower 634, 644 bodies away from one another along axis 606, into the vertically expanded configuration seen in FIGS. 16C, 24A and 24B. During vertical expansion, upper ramped surfaces 690 mate and slide against the upper ramped surfaces 755, 765 of the upper expansion slots 754, 764, and the lower ramped surfaces 692 mate and slide against the lower ramped surfaces of the lower expansion slots 714, 724. The bevels 695, 697 on each link may facilitate advancement of the link second ends 682 along ramps 717, 727, 757, 767 during vertical expansion of the spacer. During vertical expansion the distance between first and second end bodies 650, 652 continues to decrease. During vertical expansion, further outward rotation of the links is prevented by engagement of the squared-off stem portions 685 of the links with the receptacle constrictions of the upper and lower bodies.

FIG. 24B depicts the horizontally and vertically expanded configuration of the spacer 600. Spools 184 have been urged toward one another into the upper 754, 764 and lower 714, 724 expansion slots. The upper and lower head portions 686, 688 are received in the expansion slots, and into the undercuts 716, 726, 756, 766. Ramped surfaces 690 may be flush against the upper ramped surfaces of the expansion slots 754, 764, and the ramped surfaces 692 may be flush against the lower ramped surfaces of the expansion slots 714, 724. The height of the spacer 600 and the inner chamber 820 is increased with the vertical expansion, but the footprint or horizontal perimeter may remain constant during vertical expansion. When vertical expansion is complete, the insertion instrument may be removed from the spacer. Retention features 718, 758 prevent unintentional movement of the head portions out of the expansion slots under the increased compressive load resulting from the adjacent vertebrae bearing against the spacer 600. The retention features and the pockets created thereby may act as a provisional lockout to preserve the lateral and vertical expansion until addition of a secondary lockout such as locking screw 654. The inner boundaries of the expansion slots provide a physical stop to prevent any further vertical expansion. In some embodiments, a detent feature may snap or otherwise project into bore 771 above and/or bore 728 below peg 768 to prevent collapse.

In a method of the invention, the axial force provided to expand the spacer embodiments may be provided in two separate steps to expand the spacer horizontally and then vertically. In another method of the invention, the axial force may be provided continuously, resulting in smooth unbroken horizontal expansion followed immediately by vertical expansion, with no break between the expansions. In other methods, vertical expansion may be provided before horizontal expansion.

In a method of the invention, the axial force provided to expand the spacer embodiments may be provided by engagement with a screw such as lockout screw 654. This method could be advantageous if the spacer is to be implanted without addition of any bone graft material.

Following expansion of spacer 100, 400, 600, 900, 1000 or any embodiment disclosed herein, bone graft and/or other materials may be deposited into the respective inner chamber including 320, 520 or 820. Suitable materials may include allograft, autograft, demineralized bone matrix, bone chips, bone growth stimulator, bone morphogenetic protein(s), beta-tricalcium phosphate, and combinations thereof, among others. The lockout screw 654, or an insert or other locking or fastening device may be inserted and engaged with the spacer 100, 400, 600, 900, or 1000 to prevent unintentional collapse or backing out, and to keep the spacer in a rigid, stable configuration. Pedicle screws and/or rods may be implanted in addition to one or more of the spacers disclosed within to further stabilize the spine during bone ingrowth. The spacers 100, 400, 600, 900, or 1000 and their embodiments may be formed of one or more of the following materials alone or in combination, among others: stainless steel, titanium, ceramic, carbon/PEEK, and bone.

Various approaches may be implemented to implant one or more of the spacers disclosed herein in a portion of a spine to provide desired degrees of vertebral support and/or lordotic correction. In one example, a transforaminal approach may be employed, and a single, relatively small spacer implanted into the intervertebral space and expanded. In another example, a posterior approach may be employed, and two spacers implanted in the intervertebral space and expanded. In another example, a lateral approach may be employed, and a single relatively large spacer implanted, expanded horizontally and the anterior support member expanded vertically to provide asymmetrical support. In another example, an anterior approach may be employed and an asymmetric spacer implanted and expanded to provide support consistent with lordosis at that portion of the spine. In an alternative example, an anterior approach may be employed and a symmetric spacer implanted and expanded asymmetrically to provide support consistent with lordosis at that portion of the spine.

Figure 25A:
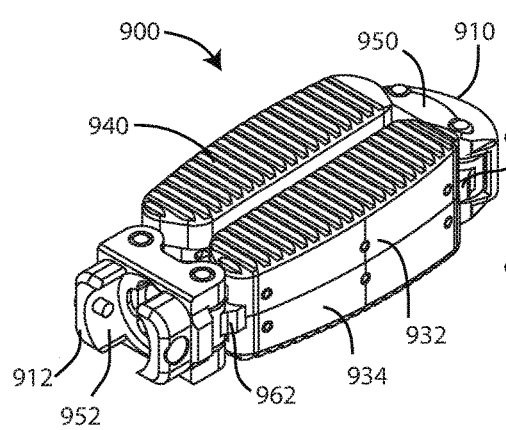
FIG. 25A is an isometric view of an embodiment of an asymmetrical expandable interbody spacer in a collapsed configuration, the interbody spacer having an integrated surface angle for spinal correction.
Figure 25B:
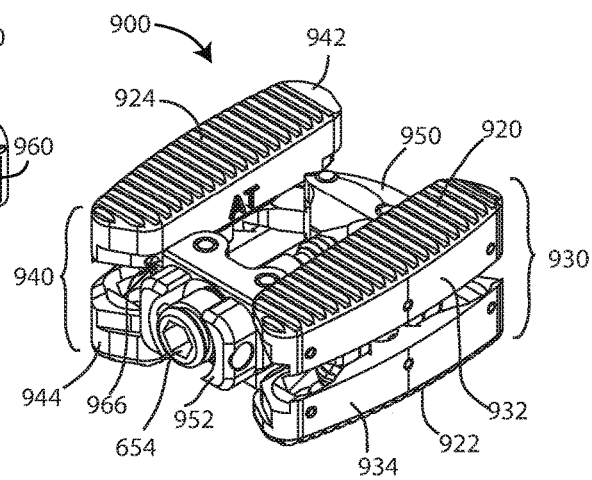
FIG. 25B is an isometric view of the spacer of FIG. 25A in a laterally and vertically expanded configuration.
Figure 25C:
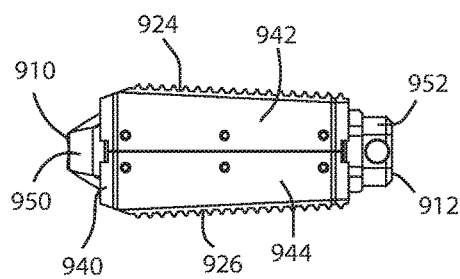
FIG. 25C is a side view of the spacer of FIG. 25A in a laterally expanded configuration, showing the surface angle for spinal correction.
Figure 25D:
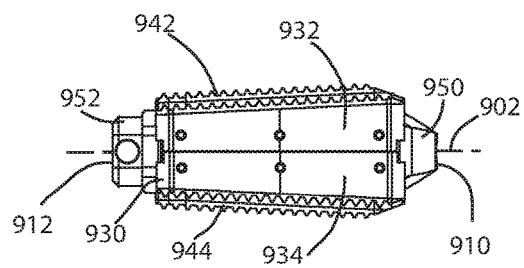
FIG. 25D is an opposite side view of the spacer of FIG. 25C.
Figure 25E:
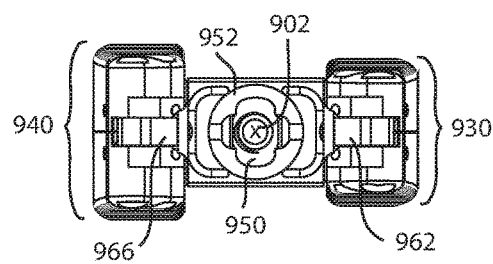
FIG. 25E is a back end view of the spacer of FIG. 25C.

Referring to FIGS. 25A-E, an interbody spacer 900 includes built in features to provide a lordotic or kyphotic correction when implanted into an intervertebral space between adjacent vertebrae. In both collapsed and expanded configurations, the spacer 900 may be bilaterally asymmetrical with respect to a vertical plane extending along a spacer axis 902, as seen in FIG. 25E, and may be bilaterally symmetrical with respect to a horizontal plane extending along spacer axis 902, as seen in FIG. 25D. The spacer 900 may include both lateral and vertical symmetric expansion capabilities. Spacer 900 has a first end 910 and a second end 912. The spacer 900 includes first and second end bodies 950, 952, which are connected to first and second support members 930, 940 by link members 960, 962, 964, 966. End bodies 950, 952 may be identical to end bodies 650, 652. Link members 960, 962, 964, 966 may be identical to link members 660, 662, 664, 666. Use of identical components may provide ease of manufacturing, assembly, and/or use. First support member 930 includes a first upper body 932 having an upper face 920 and a first lower body 934 having a lower face 922. The upper and lower bodies 932, 934 are wedge-shaped such that upper face 920 and lower face 922 are sloped between the spacer first end 910 and second end 912, relative to a horizontal plane extending along spacer axis 902. The sloped outer surfaces provide an integrated lordotic correction when the intervertebral spacer is implanted between first and second vertebral bodies of a portion of a spine. Second support member 940 includes a second upper body 942 having an upper face 924 and a second lower body 944 having a lower face 926. Second upper body 942 is vertically taller than first upper body 932; similarly, second lower body 944 is vertically taller than second lower body 944.

In the embodiment shown, support bodies 930, 940 decrease in total height between the spacer first end 910 and second end 912; and second support body 940 is thicker or taller than first support body 930. Thus when implanted between adjacent vertebral bodies, second support member 940 provides increased height support relative to first support member 930. The internal features of support bodies 930, 940 may be identical to those of support bodies 630, 640, including recessed portions/expansion slots for engagement with link members as previously described, ramps, and retention features. Interbody spacer 900 may be implanted and expanded, both laterally and vertically, as described for spacer 600. When properly positioned between two vertebral bodies, for one example with the taller first end 910 placed anteriorly, spacer 900 may provide a lordotic correction. The extent of correction provided by spacer 900 can vary. For example, spacer 900 as depicted provides an 8° angle of correction. Other embodiments may provide more or less correction ranging from 0 to 30°. In other embodiments, the height inequality between support bodies 930, 940 could be attained by differing depths of recesses in the support bodies, and/or differently sized link members or upper and/or lower bodies.

In a method of use, interbody spacer 900 may be implanted and expanded in situ according to the method described for spacer 600. An insertion and/or expansion instrument may grasp spacer 900 in the collapsed configuration, and insert the spacer between adjacent vertebral bodies in a portion of a spine. The insertion instrument, or a separate expansion instrument, may be engaged with second end body 952 and provide axial force along axis 902 to decrease the distance between first and second end bodies 950, 952. As the first and second end bodies 950, 952 are drawn together, link members 960, 962, 964, 966 pivot relative to support bodies 930, 940, and the lateral distance between first and second support bodies 930, 940 increases. As force continues to be applied along axis 902, first and second end bodies 950, 952 are drawn closer together, and the link member second ends are urged into the expansion slots within support bodies 930, 940, thus pushing upper body 932 away from lower body 934, and pushing upper body 942 away from lower body 944 to attain vertical expansion of the spacer. During vertical expansion, the two upper bodies 932, 942 may move an equal vertical distance from their respective lower bodies 934, 944. Spacer 900 may be provisionally and/or permanently locked in the horizontally and vertically expanded configuration by retention features and/or a locking screw as described for spacer 600.

Figure 26A:
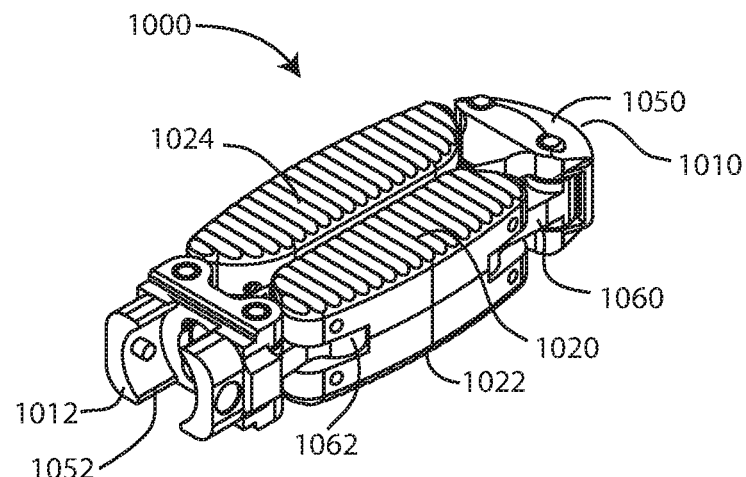
FIG. 26A is an isometric view of another embodiment of an asymmetrical expandable interbody spacer in a collapsed configuration.
Figure 26B:
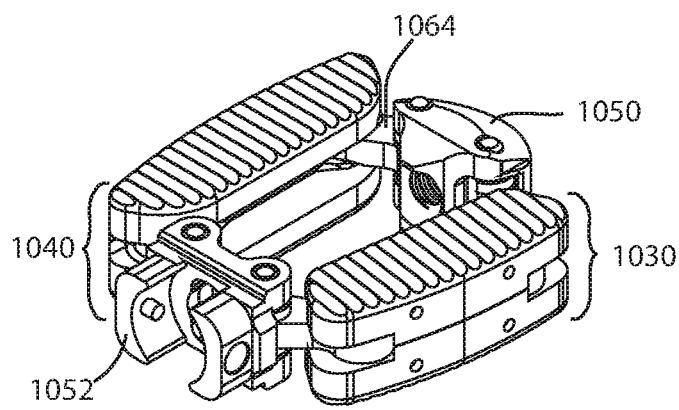
FIG. 26B is an isometric view of the spacer of FIG. 26A in a laterally expanded configuration.
Figure 26C:
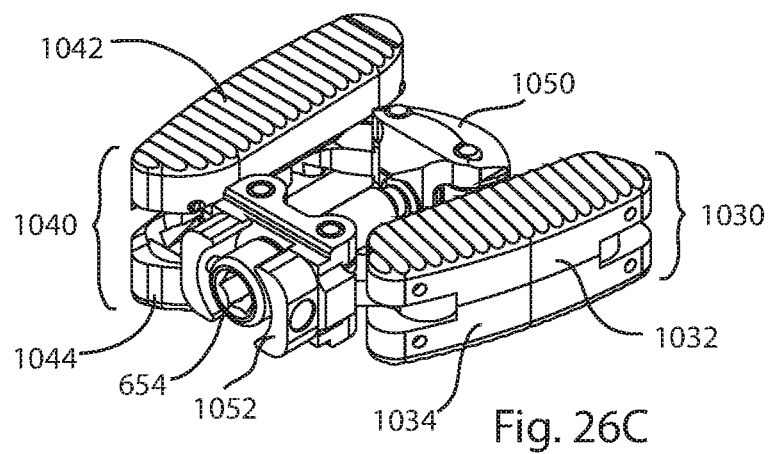
FIG. 26C is an isometric view of the spacer of FIG. 25A in a laterally and vertically expanded configuration.
Figure 27A:
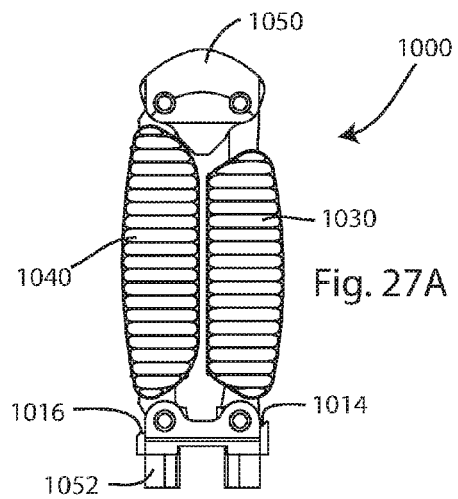
FIG. 27A is a top down view of the spacer of FIG. 26A.
Figure 27D:
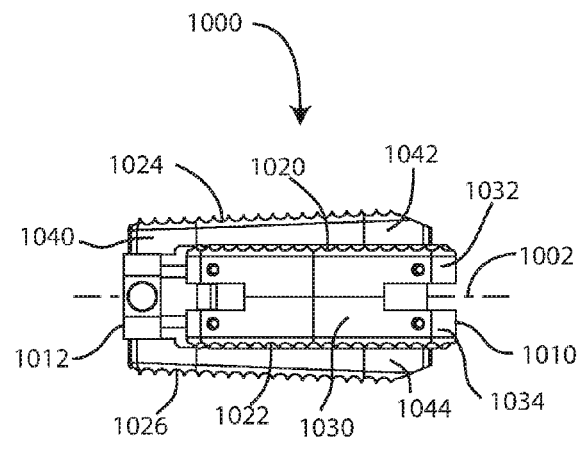
FIG. 27D is a side view of the spacer of FIG. 27C.
Figure 27B:
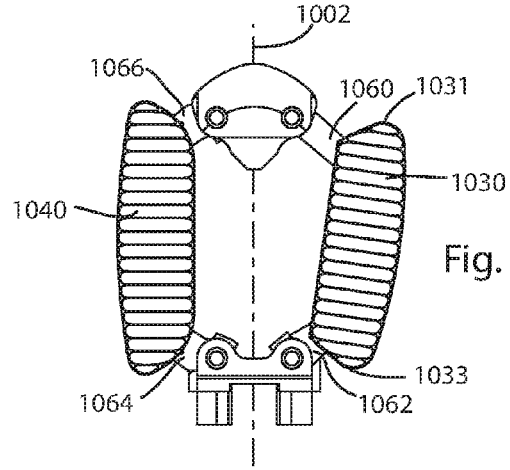
FIG. 27B is a top down view of the space of FIG. 26B.
Figure 27E:
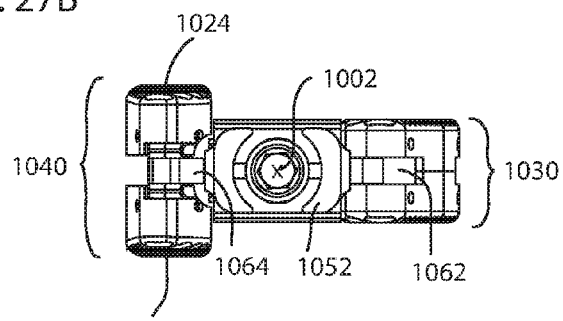
FIG. 27E is a back end view of the spacer of FIG. 27C.

Referring to FIGS. 26A-C and 27A-E, an interbody spacer 1000 includes features to provide a lordotic or kyphotic correction when implanted into an intervertebral space between adjacent vertebrae. The spacer 1000 may be bilaterally asymmetrical with respect to a vertical plane extending along a spacer axis 1002, as seen in FIG. 27E, and may be bilaterally symmetrical with respect to a horizontal plane extending along spacer axis 1002, as seen in FIG. 27D. Spacer 1000 may include both asymmetric lateral expansion and asymmetric vertical expansion capabilities.

The spacer 1000 has a first end 1010 and a second end 1012. The spacer 1000 includes first and second end bodies 1050, 1052, which are connected to first and second support members 1030, 1040 by link members 1060, 1062, 1064, 1066. End bodies 1050, 1052 may be similar to end bodies 650, 652, and include similar features such as instrument bores and stop surfaces. However first end body 1050 is asymmetric with respect to a vertical plane extending along a spacer axis 1002, and the angles of stop surfaces on opposite sides of axis 1002 may differ from one another, to allow the asymmetrical lateral expansion as seen in FIGS. 26B, 26C, 27B, and 27C. Second end body 1052 is also asymmetric with respect to a vertical plane extending along a spacer axis 1002, and the angles of stop surfaces on opposite sides of axis 1002 may differ from one another; for example a stop face 1014 is shaped differently than a stop face 1016, guiding and limiting the asymmetrical lateral expansion of support member 1030.

The spacer 1000 further comprises first and second support members 1030, 1040. During vertical expansion of spacer 1000, first support member 1030 does not expand or increase in height. Second support member 1040 may vertically increase in height. In an alternative embodiment, the relative position of the support members may be reversed such that first support member 1030 increases in height and second support member 1040 does not. First support member 1030 includes a first upper body 1032 having an upper face 1020 and a first lower body 1034 having a lower face 1022. Second support member 1040 may be identical to support member 640, and may include similar or identical features including first and second receptacles, recessed portions, and retaining features. Second support member 1040 includes a a second upper body 1042 having an upper face 1024 and a second lower body 1044 having a lower face 1026. The upper and lower bodies 1042, 1044 are wedge-shaped such that upper face 1020 and lower face 1022 are sloped between the spacer first end 1010 and second end 1012, relative to a horizontal plane extending along spacer axis 1002. The sloped outer faces provide an integrated lordotic correction when the intervertebral spacer is implanted between first and second vertebral bodies of a portion of a spine. Link members 1064, 1066 may be identical to link members 664, 666.

Figure 27C:
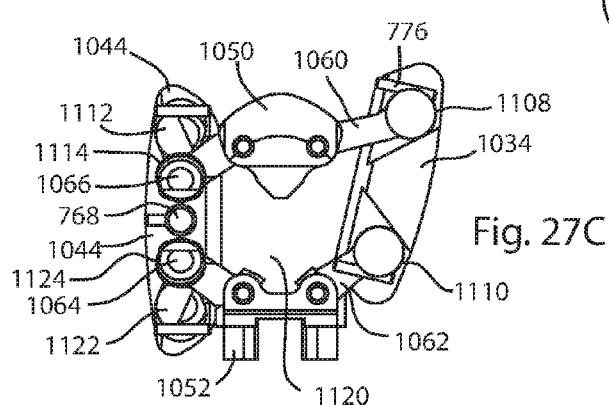
FIG. 27C is a top down partial view of the spacer of FIG. 26C with two upper support bodies absent to show the assemblage of the end bodies, links, and lower support bodies.

Referring to FIG. 27C, upper bodies 1032 and 1042 are absent in order to better view the lower bodies and link members. Link members 1060, 1062 are sized and shaped in order to permit the asymmetrical lateral expansion of first support member 1030. As seen in FIG. 27C, link member 1060 is relatively longer than link member 1062, allowing a first end 1031 of first support member 1030 to project laterally farther away from spacer axis 1002 than a second end 1033 of first support member 1030, when the spacer 1000 is laterally expanded. Upper and lower support bodies 1032, 1034 may be mirror images of each other. Each support body 1032, 1034 may include first and second receptacles 1008, 1010 for receiving links 1060, 1062 and permitting rotation of links 1060, 1062 within the receptacles during expansion of spacer 1000. Since support member 1030 does not expand vertically, expansion slots may be absent from the first and second support bodies 1032, 1034.

In an embodiment, second upper and lower bodies 1042, 1044 of vertically expandable support member 1040 may be identical to second upper and lower bodies 642, 644 of spacer 600 and/or second upper and lower bodies 942, 944 of spacer 900. Links 1064, 1066 may be identical to links 664, 666 of spacer 600 and/or links 964, 966 of spacer 900. Referring to FIGS. 27A-27C, it can be seen that in all configurations, the two end bodies 1050, 1052 are free from direct contact with one another, and free from direct contact with support members 1030, 1040. The other spacer embodiments disclosed herein may also be similarly configured.

In a method of use, spacer 1000 may be inserted and expanded according to one or more of the steps described for spacer 600 or 900. In its collapsed configuration as seen in FIG. 26A, spacer 1000 may be engaged with an insertion instrument and inserted between first and second vertebral bodies. An instrument may provide axial force along axis 1002, drawing first end body 1050 toward second end body 1052 along axis 1002, and urging links 1060, 1062, 1064, and 1066 to rotate laterally outward relative to the end bodies, thus horizontally expanding the spacer. The horizontal expansion may be asymmetrical, as illustrated in FIGS. 26B and 17A, with at least one of the first and second support bodies moving to a non-parallel juxtaposition relative to spacer axis 1006. Further force along axis 1006 may draw the first and second end bodies closer together to urge vertical expansion of second support member 1040. During the vertical expansion step, links 1064, 1066 are prevented from additional lateral rotation and slide into expansion slots 1114, 1124 on second lower body 1044 and opposing expansion slots on second upper body 1042, thus forcing second upper body 1042 vertically away from second lower body 1044. In addition, as second support member 1040 expands vertically relative to spacer axis 1002, first support member 1030 may continue to expand laterally relative to spacer axis 1002, as shown in FIGS. 26C and 27C. When the desired amount of vertical and lateral expansion is achieved, spacer 1000 may be provisionally locked in the vertically and laterally expanded configuration by retention of links 1064, 1066 in expansion slots 1114, 1124, and may also be secondarily or finally locked by engagement of locking screw 654, or another locking device.

Various features of the embodiments disclosed herein may be mixed and matched to provide additional configurations which fall within the scope of the invention. By way of non-limiting example, features and expansion capabilities of the embodiments disclosed herein may be combined to provide a symmetrical spacer embodiment providing no lordotic correction; a symmetrical spacer embodiment which provides a lordotic correction; an asymmetrical spacer embodiment providing no lordotic correction; and an asymmetrical spacer embodiment which provides a lordotic correction. One or more embodiments may be implanted together to provide the precise support and/or correction needed to restore sagittal alignment and balance.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The terms "upper" and "lower", "top" and "bottom", "front" and "back" are used as relative terms herein for ease of description and understanding. It is understood that in embodiments of the disclosure, upper and lower, top and bottom, and/or front and back entities may be reversed.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

The invention claimed is:

1. An intervertebral spacer for implantation between first and second vertebral bodies of a portion of a spine, the spacer having a first end and a second end and a first axis extending therebetween, the spacer comprising:
    a first support member comprising a first upper body and a first lower body;
    a second support member;
    a first end body located at the spacer first end and connected to the first and second support members;
    a second end body located at the spacer second end and connected to the first and second support members, wherein the axial force acts upon at least one of the end bodies to expand the spacer; and
    a plurality of individual links, each link extending between and directly connecting one of the end bodies with one of the first and second support members;
    wherein the intervertebral spacer is expandable by an application of axial force along the first axis to expand the first support member away from the second support member along a first direction, and to expand the first upper body away from the first lower body along a second direction;
    wherein the first direction is perpendicular to the first axis, and wherein the second direction is perpendicular to the first axis and to the first direction; and
    wherein each of the upper and lower bodies includes a first recess in communication with a second recess, wherein the first recess is recessed deeper within the body than the second recess.

2. The intervertebral spacer of claim 1, wherein the first direction is configured to be approximately parallel relative to the vertebral body endplates and the second direction is configured to be approximately perpendicular relative to the vertebral body endplates.

3. The intervertebral spacer of claim 1, wherein the spacer is bilaterally symmetrical relative to at least one plane extending along the first axis.

4. The intervertebral spacer of claim 1, wherein the first end body is drawn toward to the second end body along the first axis to expand the spacer.

5. The intervertebral spacer of claim 1, wherein each of the individual links rotates laterally outward relative to the end body to which it is connected, to expand the first support member away from the second support member along the first direction.

6. The intervertebral spacer of claim 5, wherein each of the individual links includes at least one stop surface, wherein the stop surface abuts one of the end bodies to limit expansion of the spacer along the first direction.

7. The intervertebral spacer of claim 1, wherein a ramp connects the first recess and the second recess, and wherein one of the individual links is urged from the first recess along the ramp into the second recess to expand the upper body away from the lower body along the second direction.

8. The intervertebral spacer of claim 1, wherein the spacer further comprises:
 a collapsed configuration in which the first support member is immediately adjacent the second support member, and the first lower body abuts the first upper body;
 a laterally expanded configuration wherein the first support member is expanded away from the second support member along the first direction;
 a vertically expanded configuration wherein the first upper body is expanded away from the first lower body along the second direction; and
 a provisional locking structure which is integrally formed into each of the first and second support members, wherein the provisional locking structure prevents unintentional collapse of the spacer out of the vertically expanded configuration.

9. The intervertebral spacer of claim 8, further comprising a supplementary locking structure, wherein the supplementary locking structure is engageable with at least one of the first and second end bodies to lock the spacer in the vertically expanded configuration.

10. The intervertebral spacer of claim 8, wherein the second support member comprises a second upper body and a second lower body;
 wherein when the spacer is in the collapsed configuration the second lower body abuts the second upper body; and
 wherein when the spacer is in the vertically expanded configuration the second upper body is expanded away from the second lower body along the second direction.

11. The intervertebral spacer of claim 1, wherein at least one of the first upper body or first lower body includes an outer surface which is sloped with respect to the first axis, the sloped outer surface providing an integrated lordotic correction when the intervertebral spacer is implanted between first and second vertebral bodies of a portion of a spine.

12. A method for implanting an intervertebral spacer between first and second vertebral bodies of a portion of a spine, the spacer having a first end and a second end and a first axis extending therebetween, the method comprising:
 inserting a spacer between first and second vertebral bodies of a portion of a spine, the spacer comprising a first support member comprising a first upper body and a first lower body, and a second support member, wherein the spacer further comprises:
  a first end body located at the spacer first end and connected to the first and second support members and a second end body located at the spacer second end and connected to the first and second support members, and
  a plurality of individual links, each link directly connecting one of the end bodies with one of the first and second support members;
 wherein each of the upper and lower bodies includes a first recess in communication with a second recess, wherein a ramp connects the first recess and the second recess;
 providing an application of axial force along the first axis, wherein the axial force moves the first support member away from the second support member along a first direction and moves the first upper body away from the first lower body along a second direction, wherein the first direction is perpendicular to the first axis, and wherein the second direction is perpendicular to the first axis and to the first direction;
 drawing the first end body toward the second end body along the first axis to expand the spacer;
 rotating each of the individual links laterally outward relative to the end body to which it is connected, to expand the first support member away from the second support member along the first direction; and
 urging at least one of the individual links from the first recess along the ramp into the second recess to expand the upper body away from the lower body along the second direction.

13. The method of claim 12, wherein the axial force along the first axis expands the spacer laterally along the first direction and then sequentially expands the spacer vertically along the second direction only after lateral expansion is completed.

14. The method of claim 12, wherein each of the individual links includes at least one stop surface, the method further comprising:
 abutting the at least one stop surface against of the end bodies to limit expansion of the spacer along the first direction.

15. The method of claim 12, wherein the spacer further comprises a collapsed configuration in which the first support member is immediately adjacent the second support member, the first lower body abuts the first upper body, the method further comprising:
 moving the first support member away from the second support member along the first direction, wherein the spacer attains a laterally expanded configuration;
 moving the first upper body away from the first lower body along the second direction, wherein the spacer attains a vertically expanded configuration; and
 provisionally locking the spacer in the vertically expanded configuration wherein locking the spacer prevents unintentional collapse of the spacer out of the vertically expanded configuration.

16. The method of claim 15, wherein the spacer further comprises a supplementary locking structure, the method further comprising:
 engaging the supplementary locking structure with at least one of the first and second end bodies to lock the spacer in the vertically expanded configuration.

17. The method of claim 15, wherein the second support member comprises a second upper body and a second lower body, the method further comprising:
moving wherein the second upper body away from the second lower body along the second direction to attain the vertically expanded configuration.

* * * * *